US011213691B2

(12) United States Patent
Volosin

(10) Patent No.: US 11,213,691 B2
(45) Date of Patent: Jan. 4, 2022

(54) AMBULATORY MEDICAL DEVICE INTERACTION

(71) Applicant: ZOLL Medical Corporation, Chelmsford, MA (US)

(72) Inventor: Kent Volosin, Mars, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 52 days.

(21) Appl. No.: 15/442,789

(22) Filed: Feb. 27, 2017

(65) Prior Publication Data

US 2018/0243578 A1 Aug. 30, 2018

(51) Int. Cl.
*A61N 1/39* (2006.01)
*A61N 1/04* (2006.01)
(Continued)

(52) U.S. Cl.
CPC ........... *A61N 1/3987* (2013.01); *A61N 1/046* (2013.01); *A61N 1/0484* (2013.01);
(Continued)

(58) Field of Classification Search
CPC .. A61N 1/3987; A61N 1/046; A61N 1/37247; A61N 1/37258; A61N 1/3621; A61N 1/3925
See application file for complete search history.

(56) References Cited

U.S. PATENT DOCUMENTS

| 3,724,455 A | 4/1973 | Unger |
| 3,922,665 A | 11/1975 | Curry et al. |

(Continued)

FOREIGN PATENT DOCUMENTS

| EP | 0707825 A2 | 4/1996 |
| EP | 0761255 A1 | 3/1997 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.

(Continued)

*Primary Examiner* — Alyssa M Alter
(74) *Attorney, Agent, or Firm* — Finch & Maloney PLLC

(57) ABSTRACT

Systems, devices, and techniques that enable medical devices to integrate and interoperate with one another are provided. In some examples, a wearable cardiac defibrillator (WCD) advantageously interoperates with an implanted pacemaker to provide a variety of benefits. For instance, in some examples, the WCD oversees execution of an anti-tachycardia (ATP) protocol by the implanted pacemaker and intervenes as needed. In other examples, the WCD drives an ATP protocol in which internal pacing pulses are provided by the implanted pacemaker under the control of the WCD. In other examples, the WCD monitors the activity of the implanted pacemaker to identify potential maintenance issues affecting the implanted pacemaker. The WCD and the implanted pacemaker may also interoperate to classify and act upon particular arrhythmia conditions.

15 Claims, 8 Drawing Sheets

(51) Int. Cl.
*A61N 1/362* (2006.01)
*A61N 1/372* (2006.01)
(52) U.S. Cl.
CPC ......... *A61N 1/3621* (2013.01); *A61N 1/3904* (2017.08); *A61N 1/3925* (2013.01); *A61N 1/37258* (2013.01)

(56) References Cited

U.S. PATENT DOCUMENTS

| | | | |
|---|---|---|---|
| 4,301,804 A | 11/1981 | Thompson et al. | |
| 4,576,170 A | 3/1986 | Bradley et al. | |
| 4,580,572 A | 4/1986 | Granek et al. | |
| 4,583,547 A | 4/1986 | Granek et al. | |
| 4,729,377 A | 3/1988 | Granek et al. | |
| 4,928,690 A | 5/1990 | Heilman et al. | |
| 4,991,217 A | 2/1991 | Garrett et al. | |
| 5,078,134 A | 1/1992 | Heilman et al. | |
| 5,225,763 A | 7/1993 | Krohn et al. | |
| 5,243,978 A | 9/1993 | Duffin, Jr. | |
| 5,306,956 A | 4/1994 | Ikeda et al. | |
| 5,348,008 A | 9/1994 | Bomn et al. | |
| 5,371,692 A | 12/1994 | Draeger et al. | |
| 5,381,798 A | 1/1995 | Burrows | |
| 5,625,291 A | 4/1997 | Brink et al. | |
| 5,741,306 A | 4/1998 | Glegyak et al. | |
| 5,929,601 A | 7/1999 | Kaib et al. | |
| 5,944,669 A | 8/1999 | Kaib | |
| 6,065,154 A | 5/2000 | Hulings et al. | |
| 6,097,982 A | 8/2000 | Glegyak et al. | |
| 6,169,387 B1 | 1/2001 | Kaib | |
| 6,253,099 B1 | 6/2001 | Oskin et al. | |
| 6,280,461 B1 | 8/2001 | Glegyak et al. | |
| 6,304,780 B1 | 10/2001 | Owen et al. | |
| 6,336,900 B1 | 1/2002 | Alleckson et al. | |
| 6,374,138 B1 | 4/2002 | Owen et al. | |
| 6,390,996 B1 | 5/2002 | Halperin et al. | |
| 6,405,082 B1 | 6/2002 | Borgenicht | |
| 6,406,426 B1 | 6/2002 | Reuss et al. | |
| 6,418,346 B1 | 7/2002 | Nelson et al. | |
| 6,442,433 B1 | 8/2002 | Linberg | |
| 6,546,285 B1 | 4/2003 | Owen et al. | |
| 6,602,191 B2 | 8/2003 | Quy | |
| 6,681,003 B2 | 1/2004 | Linder et al. | |
| 6,694,191 B2 | 2/2004 | Starkweather et al. | |
| 6,804,554 B2 | 10/2004 | Ujhelyi et al. | |
| 6,889,078 B2 | 5/2005 | Struble et al. | |
| 6,889,079 B2 | 5/2005 | Bocek et al. | |
| 6,908,437 B2 | 6/2005 | Bardy | |
| 7,088,233 B2 | 8/2006 | Menard | |
| 7,149,579 B1 | 12/2006 | Koh et al. | |
| 7,340,296 B2 | 3/2008 | Stahmann et al. | |
| 7,453,354 B2 | 11/2008 | Reiter et al. | |
| 7,476,206 B2 | 1/2009 | Palazzolo et al. | |
| 7,488,293 B2 | 2/2009 | Marcovecchio et al. | |
| 7,712,373 B2 | 5/2010 | Nagle et al. | |
| 7,831,303 B2 | 11/2010 | Rueter et al. | |
| 7,974,689 B2 | 7/2011 | Volpe et al. | |
| 7,991,460 B2 | 8/2011 | Fischell et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 8,319,632 B1 | 11/2012 | Vaisnys et al. | |
| 8,369,944 B2 | 2/2013 | Macho et al. | |
| 8,406,842 B2 | 3/2013 | Kaib et al. | |
| 8,548,584 B2 | 10/2013 | Jorgenson | |
| 8,644,925 B2 | 2/2014 | Volpe et al. | |
| 8,649,861 B2 | 2/2014 | Donnelly et al. | |
| 8,676,313 B2 | 3/2014 | Volpe et al. | |
| 8,706,215 B2 | 4/2014 | Kaib et al. | |
| 8,768,441 B2 | 7/2014 | De Zwart et al. | |
| 8,774,917 B2 | 7/2014 | Macho et al. | |
| 8,880,196 B2 | 11/2014 | Kaid | |
| 8,897,860 B2 | 11/2014 | Volpe et al. | |
| 8,904,214 B2 | 12/2014 | Volpe et al. | |
| 9,283,399 B2 | 3/2016 | Donnelly et al. | |
| 2001/0031991 A1 | 10/2001 | Russial | |
| 2002/0181680 A1 | 12/2002 | Linder et al. | |
| 2003/0004547 A1 | 1/2003 | Owen et al. | |
| 2003/0032988 A1 | 2/2003 | Fincke | |
| 2003/0095648 A1 | 5/2003 | Kaib et al. | |
| 2003/0109904 A1 | 6/2003 | Silver et al. | |
| 2003/0212311 A1 | 11/2003 | Nova et al. | |
| 2004/0049233 A1 | 3/2004 | Edwards | |
| 2004/0162510 A1 | 8/2004 | Jayne et al. | |
| 2005/0131465 A1 | 6/2005 | Freeman et al. | |
| 2005/0246199 A1 | 11/2005 | Futch | |
| 2005/0283198 A1 | 12/2005 | Haubrich et al. | |
| 2006/0095091 A1 | 5/2006 | Drew | |
| 2006/0211934 A1 | 9/2006 | Hassonjee et al. | |
| 2006/0270952 A1 | 11/2006 | Freeman et al. | |
| 2007/0129769 A1 | 6/2007 | Bourget et al. | |
| 2007/0197878 A1 | 8/2007 | Shklarski | |
| 2008/0004663 A1* | 1/2008 | Jorgenson | G09B 23/28 607/5 |
| 2008/0033495 A1 | 2/2008 | Kumar | |
| 2008/0058884 A1 | 3/2008 | Matos | |
| 2008/0097793 A1 | 4/2008 | Dicks et al. | |
| 2008/0249591 A1 | 10/2008 | Gaw et al. | |
| 2008/0287749 A1 | 11/2008 | Reuter | |
| 2008/0306560 A1 | 12/2008 | Macho et al. | |
| 2008/0306562 A1 | 12/2008 | Donnelly et al. | |
| 2008/0312709 A1 | 12/2008 | Volpe et al. | |
| 2009/0073991 A1 | 3/2009 | Landrum et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076346 A1 | 3/2009 | James et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076559 A1 | 3/2009 | Libbus et al. | |
| 2009/0138059 A1 | 5/2009 | Ouwerkerk | |
| 2009/0146822 A1 | 6/2009 | Soliman | |
| 2009/0234410 A1 | 9/2009 | Libbus et al. | |
| 2009/0264792 A1 | 10/2009 | Mazar | |
| 2009/0287120 A1 | 11/2009 | Ferren et al. | |
| 2009/0292194 A1 | 11/2009 | Libbus et al. | |
| 2009/0312650 A1 | 12/2009 | Maile et al. | |
| 2010/0052892 A1 | 3/2010 | Allen et al. | |
| 2010/0069735 A1 | 3/2010 | Berkner | |
| 2010/0076533 A1 | 3/2010 | Dar et al. | |
| 2010/0295674 A1 | 11/2010 | Hsieh et al. | |
| 2010/0298899 A1 | 11/2010 | Donnelly et al. | |
| 2010/0305462 A1 | 12/2010 | Callas et al. | |
| 2010/0312297 A1 | 12/2010 | Volpe et al. | |
| 2011/0022105 A9 | 1/2011 | Owen et al. | |
| 2011/0170692 A1 | 7/2011 | Konrad et al. | |
| 2011/0172550 A1 | 7/2011 | Martin et al. | |
| 2011/0288604 A1 | 11/2011 | Kaib et al. | |
| 2011/0288605 A1 | 11/2011 | Kaib et al. | |
| 2012/0011382 A1 | 1/2012 | Volpe et al. | |
| 2012/0112903 A1 | 5/2012 | Kaib et al. | |
| 2012/0146797 A1 | 6/2012 | Oskin et al. | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0283794 A1 | 11/2012 | Kaib et al. | |
| 2012/0289809 A1 | 11/2012 | Kaib et al. | |
| 2012/0293323 A1 | 11/2012 | Kaib et al. | |
| 2012/0302860 A1 | 11/2012 | Volpe et al. | |
| 2013/0013014 A1 | 1/2013 | Donnelly et al. | |
| 2013/0060149 A1 | 3/2013 | Song et al. | |
| 2013/0085538 A1 | 4/2013 | Volpe et al. | |
| 2013/0144355 A1 | 6/2013 | Macho et al. | |
| 2013/0218252 A1 | 8/2013 | Kaib et al. | |
| 2013/0231711 A1 | 9/2013 | Kaib | |
| 2013/0324868 A1 | 12/2013 | Kaib et al. | |
| 2013/0325078 A1* | 12/2013 | Whiting | A61N 1/36592 607/4 |
| 2013/0325096 A1 | 12/2013 | Dupelle et al. | |
| 2014/0004814 A1 | 1/2014 | Elghazzawi | |
| 2014/0031885 A1 | 1/2014 | Elghazzawi et al. | |
| 2014/0163334 A1 | 6/2014 | Volpe et al. | |
| 2014/0206974 A1 | 7/2014 | Volpe et al. | |

(56) References Cited

U.S. PATENT DOCUMENTS

| | | |
|---|---|---|
| 2014/0277243 A1 | 9/2014 | Maskara et al. |
| 2014/0303680 A1 | 10/2014 | Donnelly et al. |
| 2014/0324112 A1 | 10/2014 | Macho et al. |
| 2015/0035654 A1 | 2/2015 | Kaib et al. |
| 2015/0039039 A1 | 2/2015 | Macho et al. |
| 2015/0039042 A1 | 2/2015 | Amsler et al. |
| 2015/0039053 A1 | 2/2015 | Kaib et al. |
| 2015/0080699 A1 | 3/2015 | Kaib et al. |
| 2015/0224330 A1 | 8/2015 | Kaib et al. |

FOREIGN PATENT DOCUMENTS

| | | |
|---|---|---|
| JP | 11-149379 | 6/1999 |
| JP | 2002509472 A | 3/2002 |
| JP | 2002-514107 A | 5/2002 |
| JP | 2004-318839 | 11/2004 |
| JP | 2008-302228 A | 12/2008 |
| JP | 2008302225 A | 12/2008 |
| JP | 2009510631 A | 3/2009 |
| JP | 2009-521865 A | 6/2009 |
| JP | 2009-528909 | 8/2009 |
| JP | 2012-003311 A | 1/2012 |
| WO | 83/04171 A1 | 12/1983 |
| WO | 1997022297 A1 | 6/1997 |
| WO | 1998039061 A2 | 9/1998 |
| WO | 2000030529 A1 | 6/2000 |
| WO | 2004078259 A1 | 9/2004 |
| WO | 2007019325 A2 | 2/2007 |
| WO | 2009034506 A1 | 3/2009 |
| WO | 2009122277 A2 | 10/2009 |
| WO | 2012006524 A1 | 1/2012 |
| WO | 2012100219 A1 | 7/2012 |
| WO | 2013130957 A2 | 9/2013 |
| WO | 2014018160 A1 | 1/2014 |
| WO | 2014097035 A1 | 6/2014 |

OTHER PUBLICATIONS http://web.archive.org/web/20030427001846/http:/www.lifecor.comiimagelib/imageproduct.asp. Published by LifeCor, Inc., 2002, on a webpage owned by LifeCor, Inc.

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

International Search Report and Written Opinion from PCT/US2013/028598 dated May 9, 2013.

Zoll Medical Corporation, LifeVest Model WCD 3000 Operator's Manual, Pittsburgh, PA.

"System Guide Altrua 60 Multiprogrammable Pacemakers", Boston Scientific, 2009, 284 pages.

Dr. Cyril Yiu-Kwan Ko, "Howto Program a Pacemaker: Pacing Mode, Rate-Responsiveness, Pacing Algorithm", Heart Rhythm Refresher Course, Apr. 28, 2013, 70 pages.

Mark S. Wathen et al., "Prospective Randomized Multicenter Trial of Empirical Antitachycardia Pacing Versus Shocks for Spontaneous Rapid Ventricular Tachycardia in Patients With Implantable Cardioverter-Defibrillators", Circulation Journal of the American Heart Association, Oct. 18, 2004, 8 pages.

"Supraventricular Rhythms" ECG Pedia.ORG; <URL: http://en.ecgpedia.org/index.php?title=Supraventricular_Rhythms>, Aug. 2011, 3 pages.

"Ventricular Arrhythmias", ECGpedia, <URL: http://en.ecgpedia.org/index.php?title=Ventricular_Arrhythmias>, Feb. 2013, 2 pages.

"Pacing Codes and Modes Concepts", Software Quality Research Laboratory, <sqrl.mcmaster.ca/_SQRLDocuments/Pacing_Modes.pdf>, Nov. 6, 2015, 44 pages.

"Pacing Modes", Stimuprat, [retrieved on Sep. 12, 2016], <http://www.pacingdefibrillation.com/en/theory/pm/pacing-modes>, 9 pages.

* cited by examiner

AMBULATORY MEDICAL DEVICE INTERACTION

BACKGROUND

The present disclosure is directed to apparatus and processes through which distinct external and internal or implanted ambulatory medical devices may interoperate to monitor and/or treat patients.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

One of the most deadly cardiac arrhythmias include ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators, such as manual defibrillators or automated external defibrillators (AEDs) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

SUMMARY

According to one example an ambulatory medical device is provided. The ambulatory medical device includes at least one therapy electrode configured to couple externally to a skin of a patient and to provide one or more transthoracic therapeutic stimulation pulses to a heart of the patient; at least one sensing electrode configured to couple externally to the skin of the patient and to acquire electrocardiogram (ECG) signals from the patient; and at least one processor coupled to the at least one therapy electrode and the at least one sensing electrode. The at least one processor is configured to process the ECG signals from the patient to detect a tachycardia condition in the heart of the patient; determine, in response to detecting the tachycardia condition, whether an implanted pacemaker restores the heart of the patient to a normal condition within a predetermined period; and provide the one or more transthoracic therapeutic stimulation pulses to the heart of the patient in response to determining that the implanted pacemaker failed to restore the heart of the patient to the normal condition within the predetermined period.

In the ambulatory medical device, the one or more transthoracic therapeutic stimulation pulses may include at least one defibrillation pulse. The at least one processor may be further configured to transmit an alert in response to the implanted pacemaker having failed to restore the heart of the patient to the normal condition within the predetermined period. The ambulatory medical device may further include an interface configured to communicate with the implanted pacemaker. The at least one processor may be further configured to signal the implanted pacemaker to enter an anti-tachycardia pacing (ATP) mode in response to detecting the tachycardia condition. The at least one processor may be configured to determine whether the implanted pacemaker restored the heart of the patient to the normal condition at least in part by comparing the ECG signals to a baseline of the heart of the patient recorded during an initial fitting of the ambulatory medical device to the patient. The at least one processor may be configured to determine whether the implanted pacemaker restored the heart of the patient to the normal condition at least in part by identifying at least one internal pacing pulse provided by the implanted pacemaker and determining whether the at least one internal pacing pulse resulted in myocardial depolarization.

In the ambulatory medical device, the at least one processor may be further configured to detect a presence of the implanted pacemaker within the patient. The at least one processor may be configured to detect the presence of the implanted pacemaker within the patient at least in part by processing ECG data representative of the ECG signals to identify at least one pacing pulse spike. The ambulatory medical device, may further include an electromagnet coupled to the at least one processor. The at least one processor may be configured to detect the presence of the implanted pacemaker within the patient at least in part by energizing the electromagnet and processing ECG data representative of the ECG signals to match a heart rate of the patient to at least one of a magnet rate of the implanted pacemaker, a noise reversion rate of the implanted pacemaker, and an interference rate of the implanted pacemaker.

The ambulatory medical device may further include an interface configured to communicate with the implanted pacemaker. The at least one processor may be further configured to transmit an instruction to reconfigure the implanted pacemaker via the interface in response to the implanted pacemaker having failed to restore the heart of the patient to the normal condition within the predetermined period. In the ambulatory medical device, the instruction to reconfigure may include an instruction to alter at least one characteristic of at least one internal pacing pulse. The at least one characteristic may include at least one of a pulse waveform, a pulse energy level, a pulse rate, and a pulse width.

According to another example, an ambulatory medical device is provided. The ambulatory medical device includes at least one therapy electrode configured to couple externally to a skin of a patient and to provide one or more transthoracic therapeutic stimulation pulses to a heart of the patient; at least one sensing electrode configured to couple externally to the skin of the patient and to acquire electrocardiogram (ECG) signals from the patient; and at least one processor coupled to the at least one therapy electrode and the at least one sensing electrode. The at least one processor is configured to process the ECG signals from the patient to detect a pattern in the ECG signals indicative of an arrhythmia condition; monitor the patient transcutaneously via the at least one sensing electrode for one or more internal pacing pulses provided by an implanted pacemaker to the heart of the patient; detect the one or more internal pacing pulses within a first predetermined time period; and record the pattern as being untreatable by the ambulatory medical device within the first predetermined time period in response to detecting the one or more internal pacing pulses, thereby preventing provision of the one or more transthoracic therapeutic stimulation pulses.

In the ambulatory medical device, the at least one processor may be further configured to detect an absence of internal pacing pulses within a second predetermined time period; and record the pattern as being treatable within the second predetermined time period in response to detecting the absence of internal pacing pulses. The at least one processor may be further configured to initiate a treatment sequence comprising providing one or more alerts regarding an impending treatment to the patient in response to recording the pattern as being treatable. According to another example, an ambulatory medical device is provided. The ambulatory medical device includes at least one therapy electrode configured to couple externally to a skin of a patient and to provide one or more therapeutic stimulation pulses to a heart of the patient; an interface configured to communicate with an implanted pacemaker implanted within the patient; and at least one processor coupled to the at least one therapy electrode and the interface. The at least one processor is configured to receive, from the implanted pacemaker via the interface, atrial ECG data descriptive of atrial heart activity, receive, from the implanted pacemaker via the interface, ventricular ECG data descriptive of ventricular heart activity, and identify an arrhythmia condition based on the atrial ECG data and the ventricular ECG data.

In the ambulatory medical device, the atrial ECG data and the ventricular ECG data may indicate atrioventricular dissocation. The at least one processor may be configured to identify the arrhythmia condition as a tachycardia condition where the atrial ECG data indicates a beat rate between 60 beats per minute and 100 beats per minute and the ventricular ECG data indicates a beat rate between 110 beats per minute and 250 beats per minute. The at least one processor may be configured to determine, in response to detecting the tachycardia condition, whether the implanted pacemaker restored the heart of the patient to a normal condition within a predetermined period and provide the one or more therapeutic stimulation pulses to the heart of the patient in response to determining that the implanted pacemaker failed to restore the heart of the patient to the normal condition within the predetermined period. The predetermined period may be 60 seconds. The at least one processor may be configured to identify the arrhythmia condition as a fibrillation condition where the atrial ECG data indicates a beat rate between 60 beats per minute and 100 beats per minute and the ventricular ECG data indicates a beat rate between 300 beats per minute and 600 beats per minute; and provide, in response to identifying the fibrillation condition, the one or more therapeutic stimulation pulses to the heart of the patient via the at least one therapy electrode. The at least one processor may be configured to identify the arrhythmia condition as a supraventricular tachycardia condition where the atrial ECG data indicates a beat rate between 150 beats per minute and 250 beats per minute and the ventricular ECG data indicates a beat rate between 150 beats per minute and 250 beats per minute.

According to another example, an ambulatory medical device is provided. The ambulatory medical device includes a memory storing at least one ECG signal pattern indicative of at least one associated condition of an internal cardiac device that requires maintenance of the internal cardiac device; at least one sensing electrode configured to couple externally to a skin of a patient and to acquire ECG signals from the patient; and at least one processor coupled to the memory and the at least one sensing electrode. The at least one processor is configured to process the ECG signals to identify the at least one ECG signal patterns within the ECG signals; and provide a notification of the at least one associated condition to the patient.

In the ambulatory medical device, the at least one ECG signal pattern may include an ECG signal pattern indicating a series of pacing pulses provided at a battery pacing rate of the internal cardiac device and the at least one associated condition may include a runtime of a battery of the internal cardiac device being below a predetermined value. The at least one ECG signal pattern may include an indication of a pacing pulse that failed to result in myocardial depolarization and the at least one associated condition may include at least one of lead displacement and wire fracture. The at least one ECG signal pattern may include an ECG signal pattern lacking a pacing pulse and the at least one associated conditions may include an oversensing internal cardiac device. The at least one ECG signal pattern may include an ECG signal pattern indicating one or more unnecessary pacing pulses and the at least one associated condition may include an undersensing internal cardiac device.

According to another example, an ambulatory medical device is provided. The ambulatory medical device includes at least one therapy electrode configured to couple externally to a skin of a patient and to provide one or more subtherapeutic stimulation pulses to a chest wall of the patient and one or more transthoracic therapeutic stimulation pulses to a heart of the patient; at least one sensing electrode configured to couple externally to the skin of the patient and to acquire ECG signals from the patient; and at least one processor coupled to the at least one therapy electrode and the at least one sensing electrode. The at least one processor is configured to process the ECG signals from the patient to detect a tachycardia condition in the heart of the patient and trigger an implanted pacemaker to provide one or more internal pacing pulses to the heart of the patient at least in part by providing the one or more subtherapeutic stimulation pulses to the chest wall of the patient.

In the ambulatory medical device, the at least one processor may be further configured to determine whether the implanted pacemaker, in providing the one or more internal pacing pulses to the heart of the patient, restored the heart of the patient to a normal condition within a predetermined period and provide the one or more transthoracic therapeutic stimulation pulses to the heart of the patient in response to determining that the implanted pacemaker failed to restore the heart of the patient to the normal condition within the predetermined period. Each internal pacing pulse of the one or more internal pacing pulses may correspond to one subtherapeutic stimulation pulse of the one or more subtherapeutic stimulation pulses. The at least one processor may be further configured to determine a tachycardia rate of the tachycardia condition and trigger the implanted pacemaker to provide the one or more internal pacing pulses to the patient at a rate between 80% and 90% of the tachycardia rate. The one or more internal pacing pulses may include between 5 and 20 internal pacing pulses. The at least one processor may be further configured to detect a presence of the implanted pacemaker within the patient. The at least one processor may be configured to detect the presence of the implanted pacemaker within the patient at least in part by processing ECG data representative of the ECG signals to identify at least one pacing pulse spike. The ambulatory medical device may further include an electromagnet coupled to the at least one processor. The at least one processor may be configured to detect the presence of the implanted pacemaker within the patient at least in part by energizing the electromagnet and processing ECG data representative of the ECG signals to match a heart rate of the patient to at least one of a magnet rate of the implanted pacemaker, a noise reversion rate of the implanted pacemaker, and an interference rate of the implanted pacemaker.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
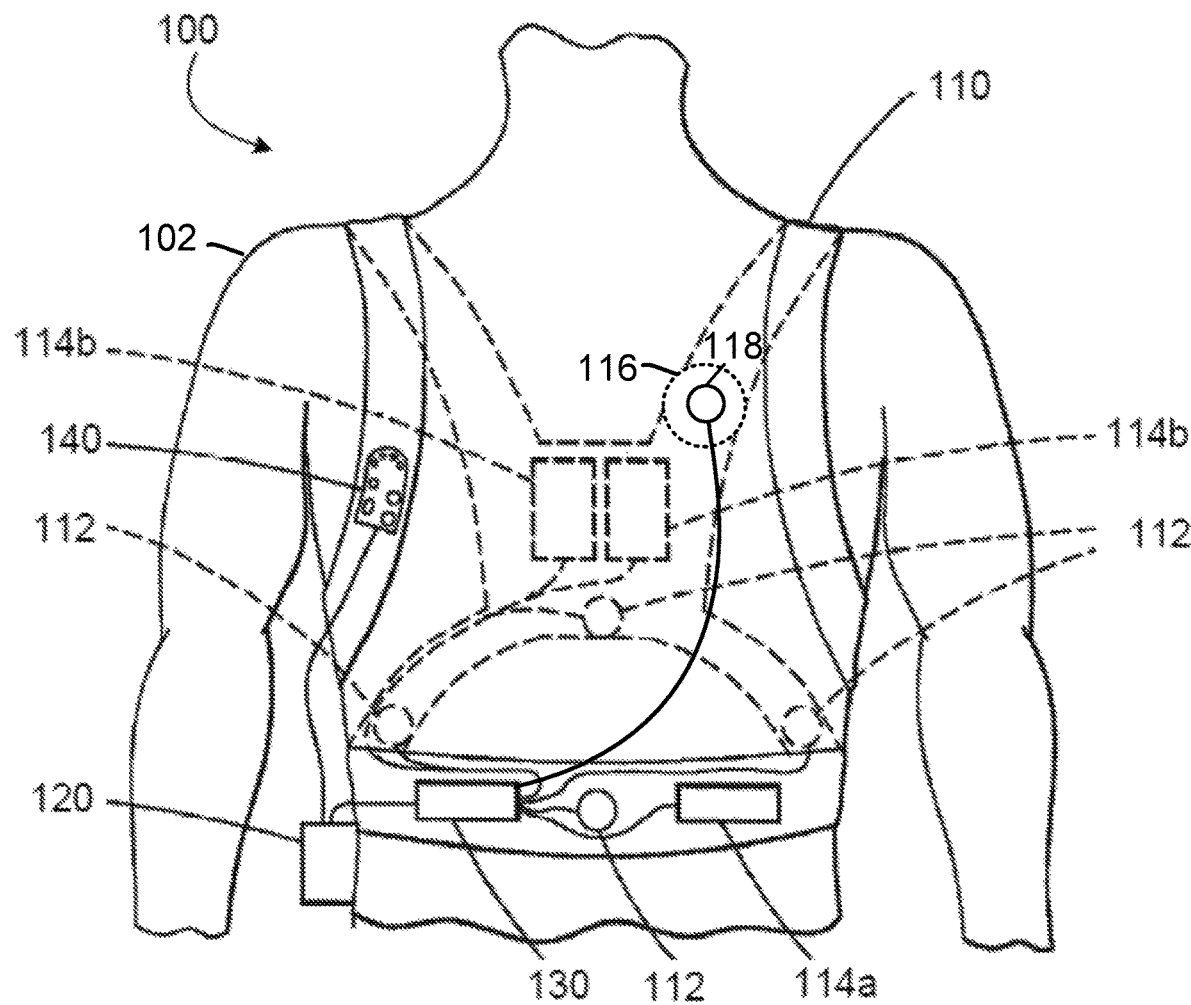
FIG. 1 depicts a wearable, ambulatory, external medical device in accordance with at least one example disclosed herein.

This disclosure relates to systems, devices, and techniques that integrate the operations of external medical devices with implantable medical devices. These systems, devices, and techniques may be employed, for instance, by a wearable cardiac defibrillator (WCD) to transcutaneously monitor a patient and a pacemaker implanted within the patient and in some instances to control the pacemaker. Additionally or alternatively, in some examples, the WCD intervenes to provide therapy to the patient, where the pacemaker is unable to successfully treat the patient. For example, as noted in detail below, the WCD may interact with an implantable medical device within a patient in order to influence one or more of a pacing mode, multiple rate response settings, electrode polarity, maximum and minimum pacing rates, output energy (e.g., output pulse width and/or output current), sense amplifier sensitivity, refractory periods, calibration information, rate response attack (e.g., acceleration of rate) and decay (e.g., deceleration or rate), onset detection criteria, and other implanted device parameter settings. For diagnostic purposes, for example, it is also desirable for the WCD to retrieve from the implanted device information regarding the implanted device's operational status, which can then be provided to a physician, technician, or other surrogate.

Pacemakers can detect tachycardia and provide patients with anti-tachycardia pacing (ATP). However, an episode of tachycardia that is not successfully treated may degrade into atrial fibrillation (AF) or ventricular fibrillation (VF). AF and VF are potentially life threatening arrhythmias and are conventionally treated by provision of one or more defibrillating ECG pulses. Implantable cardioverter defibrillators (ICDs) are capable of providing such defibrillating pulses, but many traditional pacemakers are not. Thus, a WCD configured to monitor ATP provided by a traditional pacemaker and defibrillate a patient if needed can save patient lives.

In some examples, a WCD is configured for prophylactic use in conjunction with an implanted pacemaker configured to execute anti-tachycardia pacing. In these examples, the WCD includes may include an electromagnet and use the electromagnet to detect the presence of the implanted pacemaker. The WCD detects tachycardia conditions suffered by the patient and monitors the implanted pacemaker and the patient's heart while the tachycardia conditions persist. If the WCD determines that the implanted pacemaker's execution of ATP is not resulting in capture (e.g., myocardial depolarization) or that the patient's heart has not returned to a normal condition (e.g., normal sinus rhythm) within a predetermined time period, the WCD intervenes by executing any of a variety of preprogrammed actions. Examples of these preprogrammed actions include transmitting one or more notifications to the patient, bystander, or other recipients (including remote recipients), altering characteristics of the ATP pulses, and providing one or more defibrillation pulses to the patient.

In some examples, a WCD is configured to use pacing pulses issued by an implanted pacemaker to discriminate between true arrhythmias and artifacts that appear to be arrhythmias. For example, when executing according to this configuration, the WCD may identify an arrhythmia based on ECG signals acquired transcutaneously that are, in reality, produced by noise, movement artifacts, or some source other than the patient's heart. In these situations, an implanted pacemaker may be in a better position to determine whether a true arrhythmia exists. To leverage this fact, in some examples a WCD monitors the patient for internal pacing pulses provided by the implanted pacemaker. Where internal pacing pulses are detected, the WCD records the arrhythmia that it detected as presently untreatable by the WCD. Where internal pacing pulses are not detected, despite the present of the implanted pacemaker, the WCD records the arrhythmia as treatable by the WCD. Where the arrhythmia is treatable, the WCD may execute a treatment sequence, which may include provision of alerts to warn the patient or bystander of an impending treatment, and issuance of one or more therapeutic shocks to restore the patient's heart to a normal condition.

In some examples, a WCD is configured to use atrial and ventricular contraction rates to identify arrhythmias. In these examples, the implanted pacemaker is a dual chamber pacemaker with both atrial and ventricular leads. The implanted pacemaker transmits ECG data descriptive of atrial and ventricular activity to the WCD. The WCD receives the ECG data and determines, for example, that an arrhythmia is present where the atrial rate is different from the ventricular rate (e.g., where AV dissociation is evident). The WCD may further classify the arrhythmia as tachycardia (e.g., where the atrial rate is between 60 and 100 beats per minute (bpm) and the ventricular rate is between 110 and 250 bpm) or fibrillation (e.g., where the atrial rate is between 60 and 100 bpm and the ventricular rate is between 300 and 600 bpm). The WCD may also classify the arrhythmia as supraventricular tachycardia where AV dissociation is not evident (e.g., where the atrial rate and the ventricular rate are each between 150 and 250 bpm). Further in these examples, the WCD may supplement the pacemaker by providing one or more pacing pulses where the patient's heart does not return to a normal condition within a predetermined period of time. The WCD may also provide one or more defibrillation pulses where a fibrillation condition is detected.

In some examples, a WCD is configured to monitor a patient's cardiac activity and to drive ATP pacing pulses provided by an implanted pacemaker. When executing according to some of these configurations, the WCD processes ECG signals acquired transcutaneously from the patient to detect arrhythmias and provides a subtherapeutic stimulation pulse to the chest wall of the patient for each pacing pulse to be provided by the implanted pacemaker. In some examples, each subtherapeutic stimulation pulse can have a duration in a range of about 25-60 milliseconds. In one implementation, a subtherapeutic stimulation pulse has a duration of approximately 40 milliseconds, a rectangular waveform, and a current within an approximate range of 1 to 50 milliamps. In other implementations, subtherapeutic stimulation pulses can have waveforms other than a rectangular waveform, e.g., waveforms where there may be a predetermined amount of a leading or falling slope to the shape of the pulse. The implanted pacemaker, which may be operating in triggered mode, detects each subtherapeutic stimulation pulse and, in response to each, provides a corresponding internal pacing pulse. The WCD may be configured to detect the presence of the implanted pacemaker and may include an electromagnet for this purpose. The WCD may also provide therapeutic stimulation pulses to the heart of the patient where the implanted pacemaker is unable to restore the patient's heart to a normal condition with a predetermined time period.

In some examples, a WCD or an MCT device is configured to monitor ICD operation for potential maintenance issues with the ICD. In these examples, the WCD or MCT device acquires ECG signals from a patient with an ICD and compares the acquired signals to a set of signal benchmarks that indicate conditions of an ICD that are addressable by maintenance of the ICD. Examples of these maintenance conditions include a low battery, ineffective pacing pulses, omission of needed pulses, and provision of unneeded pulses. In some examples, the WCD or MCT may attempt to remediate the maintenance conditions by reconfiguring the ICD. For example, the WCD or MCT may adjust the characteristics of ineffective pacing pulses and pacing pulses provided by a ICD with a low battery.

The systems, devices, and techniques disclosed herein provide several advantages over conventional technology. For instance, some examples enable pacemakers incapable of providing defibrillating pulses to safely provide ATP to patients experiencing tachycardia. In some examples, a WCD can avoid unnecessary transcutaneous pulses by monitoring the activity of an implanted pacemaker, thereby avoiding patient discomfort. In some examples, a WCD receives enhanced cardiac data from a dual chambered implanted pacemaker, thereby gaining additional insight into a patient condition. In these examples, the WCD may more appropriately provide or withhold therapy based on the enhanced cardiac data. The enhanced cardiac data can be transmitted to a remote server for further review and analysis, and, in some cases, technicians may use the data and the remote server to prepare reports that may be delivered to physicians within a network.

In some examples, a WCD can interoperate with an implanted pacemaker to drive the pacemaker's operation, which can be particular beneficial where the implanted pacemaker is operating in an anomalous manner. In some examples, a WCD monitors the operation of an implanted pacemaker to detect present or potential issues that require maintenance and to notify a predetermined targeted recipient (e.g., technical support personnel, caregiver, a relative, or a patient surrogate) of the present or potential maintenance issues. These and other functions of medical devices can be enhanced using the systems, devices, and techniques disclosed herein.

Example Medical Devices

The teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device is capable of continuous (e.g., substantially or nearly continuous) use by the patient. In some implementations, the continuous use may be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, heart sounds, etc.) and/or non-cardiac information (e.g., blood oxygen, the patient's temperature, glucose levels, tissue fluid levels, and/or lung sounds). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung sounds (e.g., using microphones and/or accelerometers), breath sounds, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's electrocardiogram (ECG) information, heart sounds (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart sounds (e.g., using accelerometers or microphones), lung sounds, breath sounds, sleep related parameters (e.g., snoring, sleep apnea), tissue fluids, among others.

Example Wearable Medical Devices

FIG. 1 illustrates an example medical device 100 that is external, ambulatory, and wearable by a patient 102, and configured to use one or more of the systems, devices, and techniques described herein to integrate and/or interoperate with an implantable medical device 116, such as a pacemaker, implanted within the patient 102. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic stimulation pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes) one or more therapy electrodes 114, a medical device controller 120, a connection pod 130, a patient interface pod 140, a belt 150, an electromagnet 118, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and therapy electrodes 114 can be included on a single integrated patch and adhesively applied to the patient's body.

The sensing electrodes 112 can be configured to detect one or more cardiac signals. Examples of such signals include ECG signals and/or other sensed cardiac physiological signals from the patient. In some examples, the sensing electrodes 112 are included in a housing or coupled to an assembly that includes additional sensors, such as accelerometers. In these examples, the sensing electrodes 112 and associated sensors can also be configured to detect other types of patient physiological parameters, such as heart sounds, tissue fluid levels, lung sounds, respiration sounds, patient movement, etc. Example sensing electrodes 112 include a metal electrode with an oxide coating such as tantalum pentoxide electrodes, as described in, for example, U.S. Pat. No. 6,253,099 titled "Cardiac Monitoring Electrode Apparatus and Method," the content of which is incorporate herein by reference. Example sensing electrodes 112 also include conductive electrodes with a foundational layer (e.g., made of foam), an electrically conductive element (e.g., made of tin, silver-silver chloride, etc.), and an electrolytic layer (e.g., made of hydrogel) that electrically couples the conductive element to the patient's skin. This electrolytic layer may be applied manually by a healthcare provider or may be disposed automatically by a gel dispenser positioned near the conductive electrode.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless steel electrodes that include, in certain implementations, one or more conductive gel deployment devices configured to deliver conductive gel to the metal electrode prior to delivery of a therapeutic shock.

In some examples, the electromagnet 118 is coupled to and controllable by the medical device controller 120. In these examples, the medical device controller 120 can energize the electromagnet 118 to cause the pacemaker 116 to enter a default or preprogrammed pacing mode that depends on the model of the pacemaker 116. Additionally or alternatively, in some examples, the medical device controller 120 may communicate with the pacemaker 116 using other mechanisms, such as radio frequency or other wireless media.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device 100.

WMD/WCD Controller Description

Figure 2:
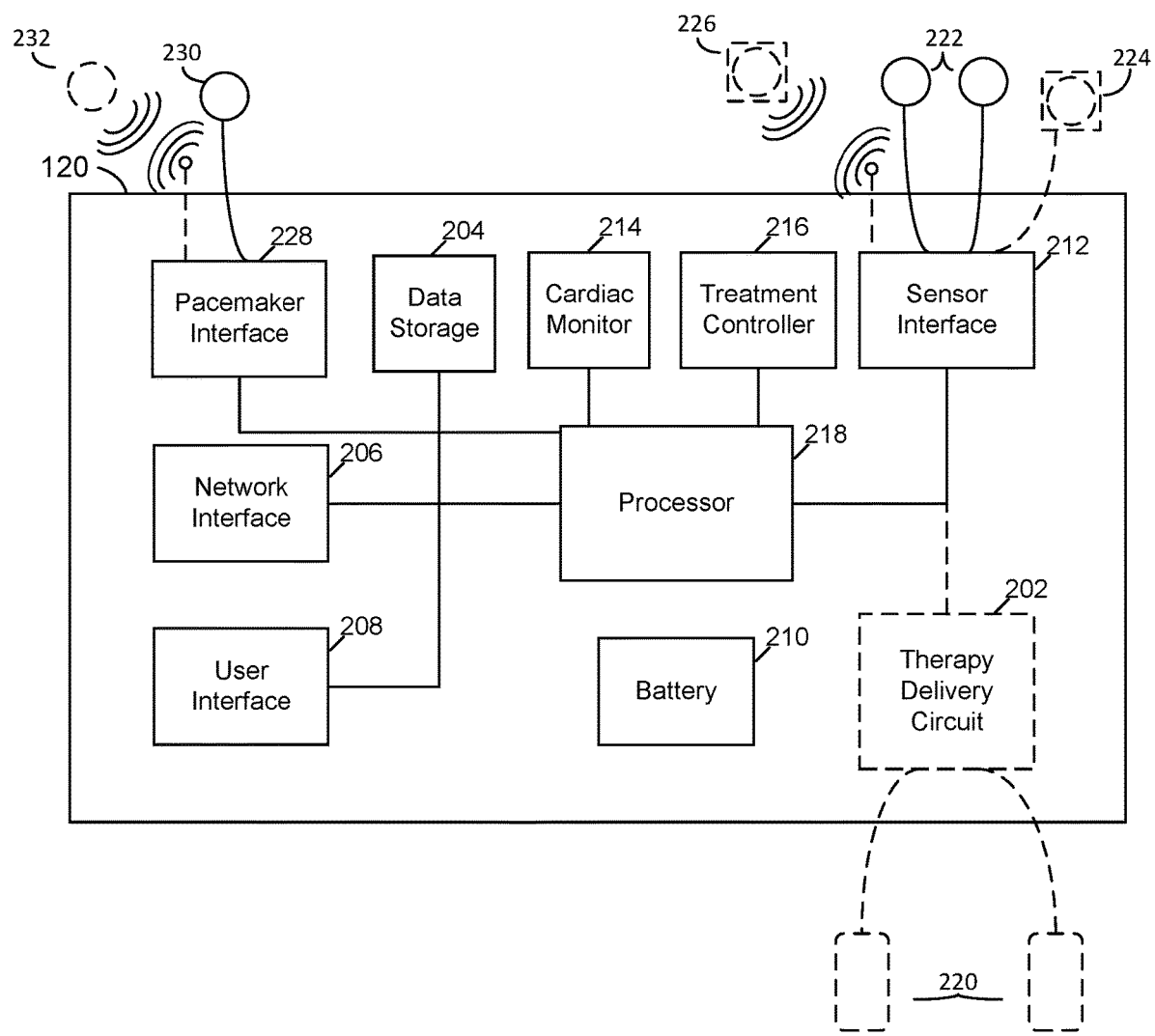
FIG. 2 depicts an arrangement of components of a medical device controller in accordance with at least one example disclosed herein.
Figure 3:
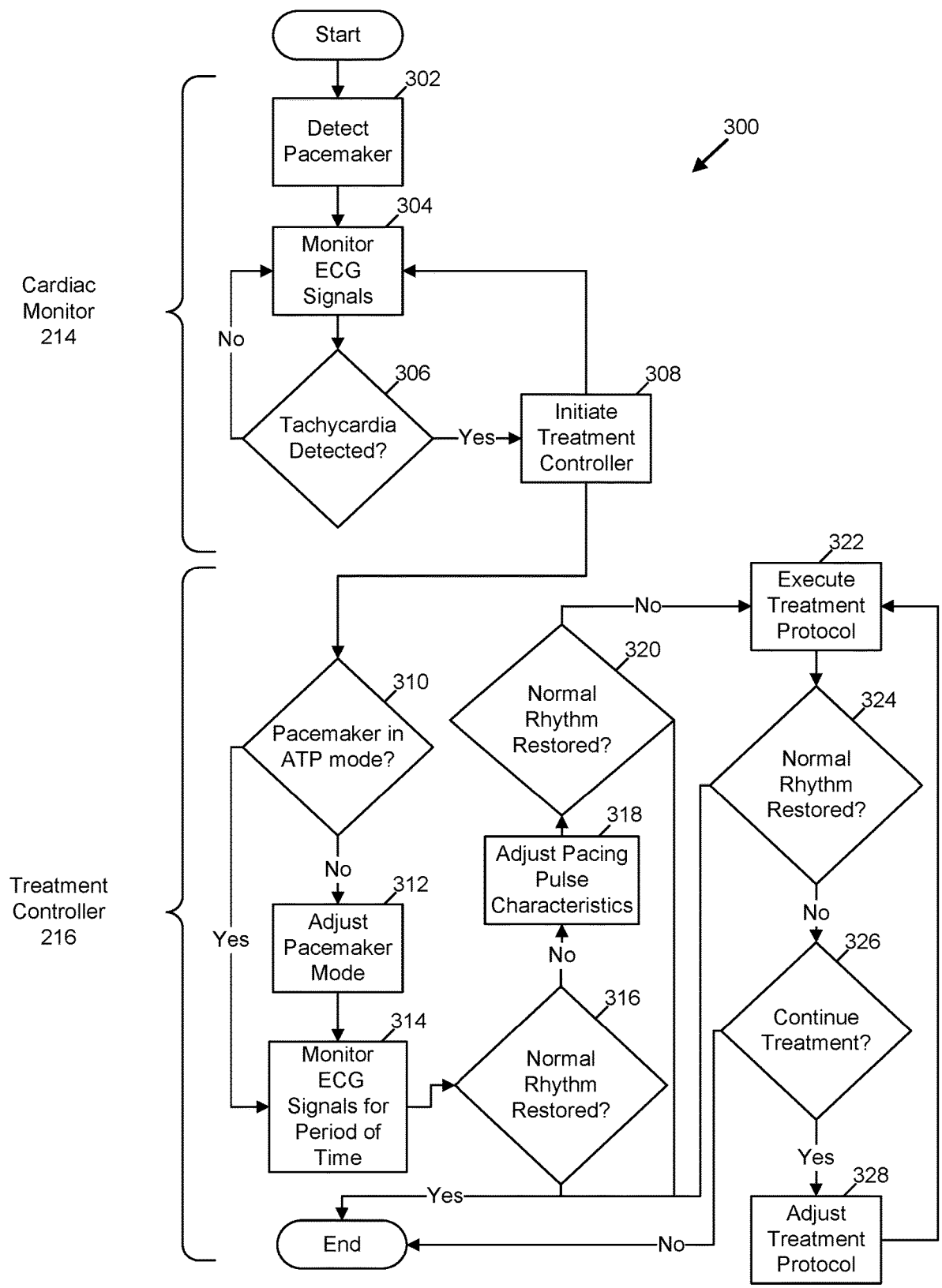
FIG. 3 depicts a monitoring and treatment process in accordance with at least one example disclosed herein.
Figure 4:
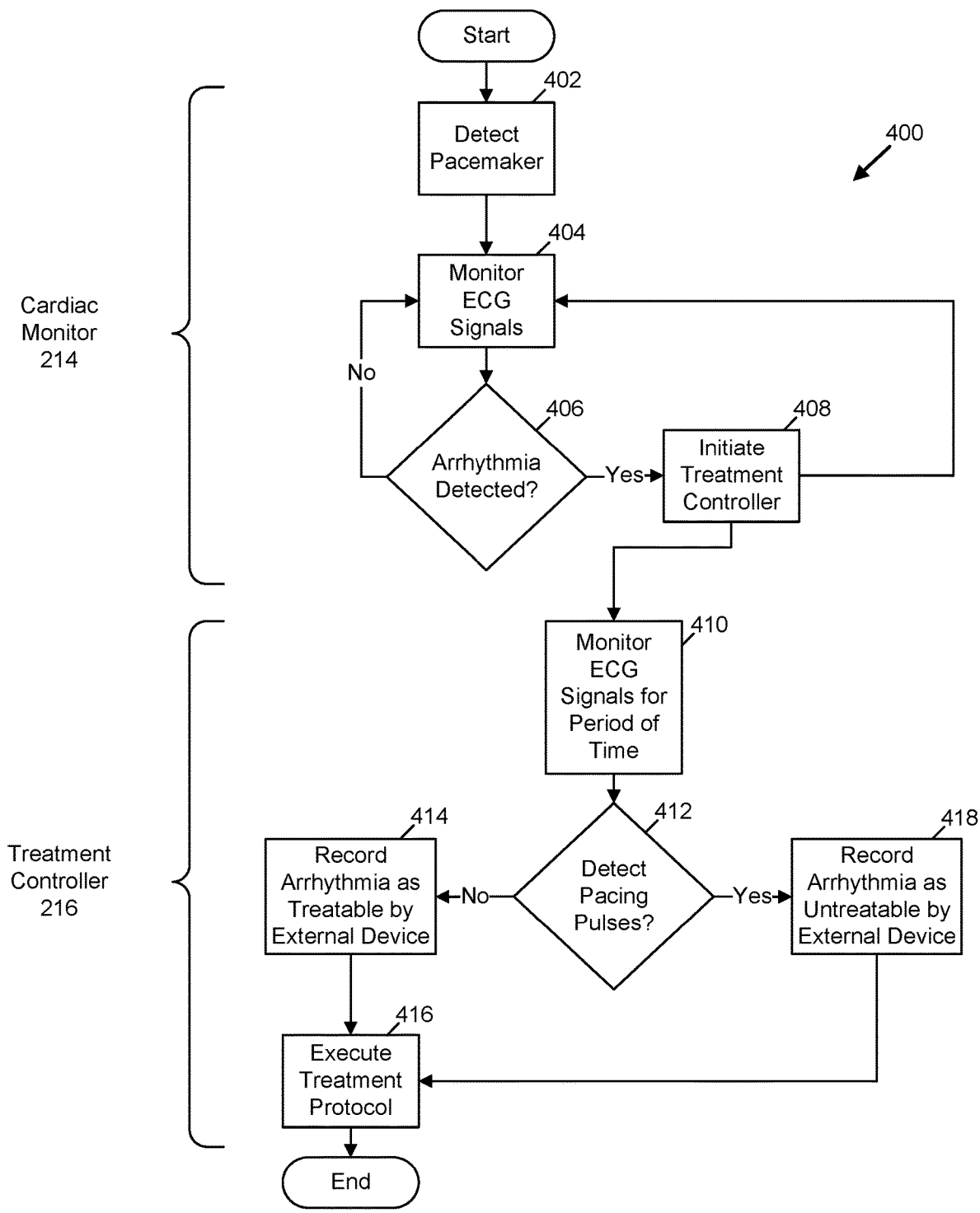
FIG. 4 depicts another monitoring and treatment process in accordance with at least one example disclosed herein.
Figure 5:
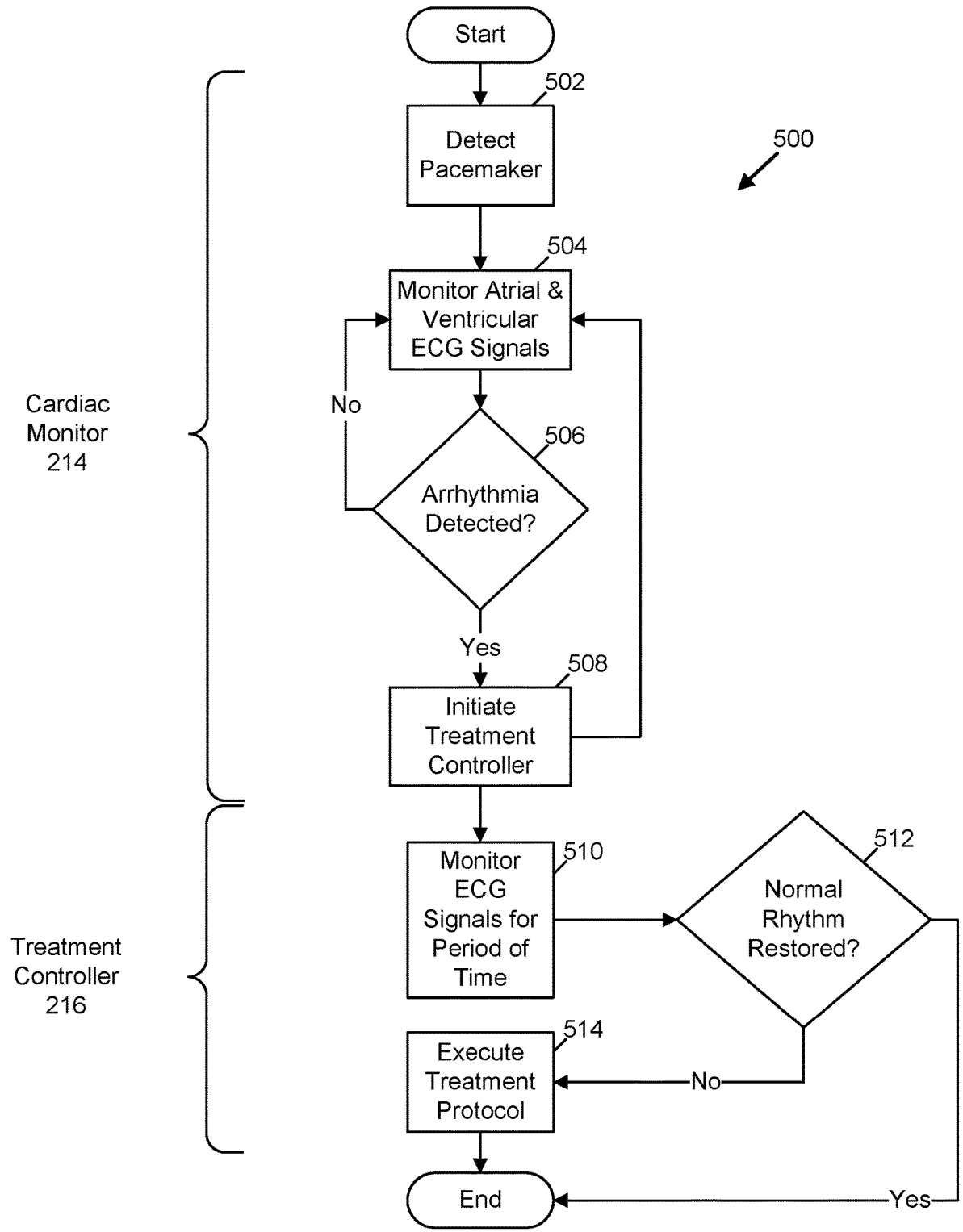
FIG. 5 depicts another monitoring and treatment process in accordance with at least one example disclosed herein.
Figure 6:
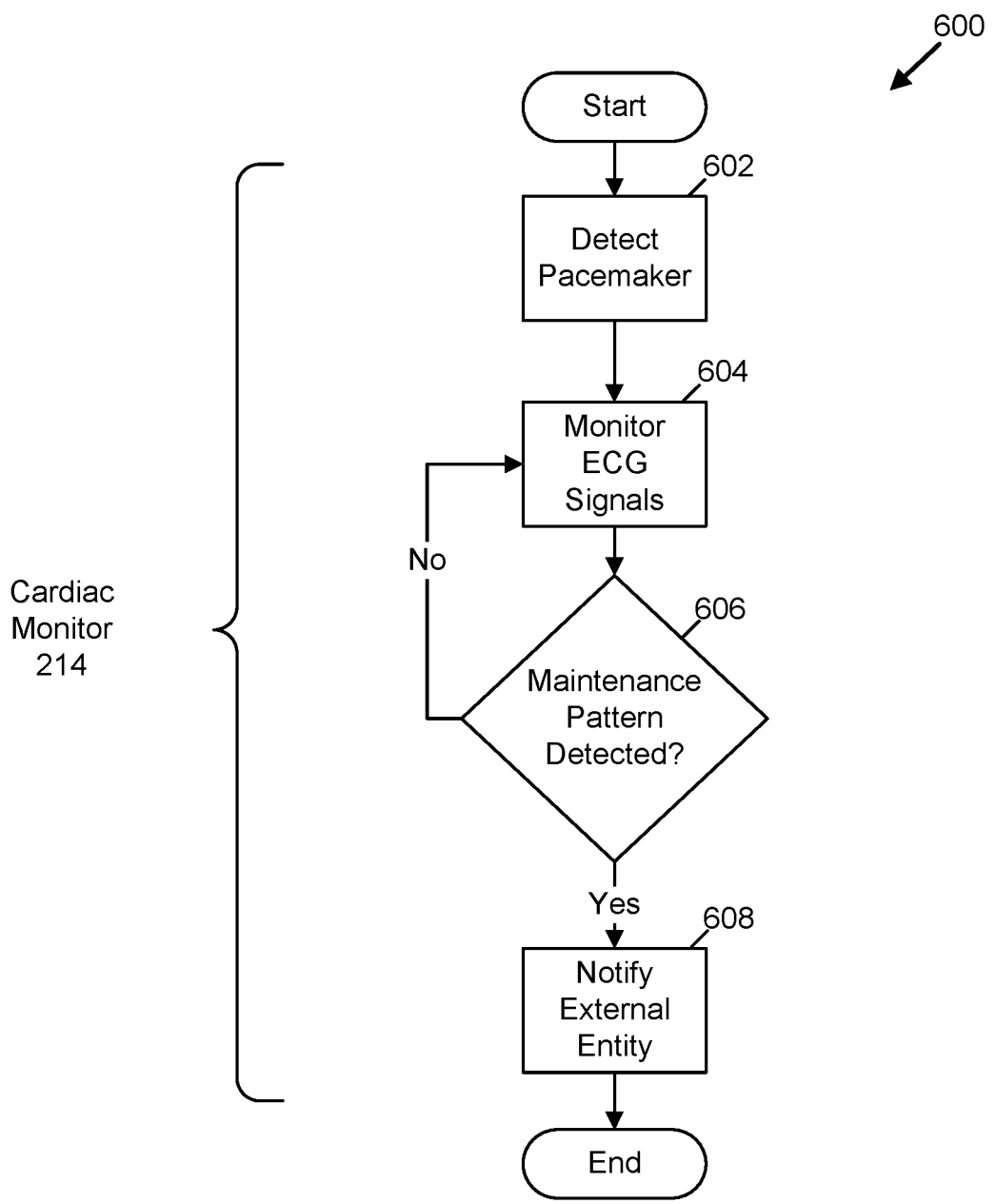
FIG. 6 depicts a monitoring process in accordance with at least one example disclosed herein.
Figure 7:
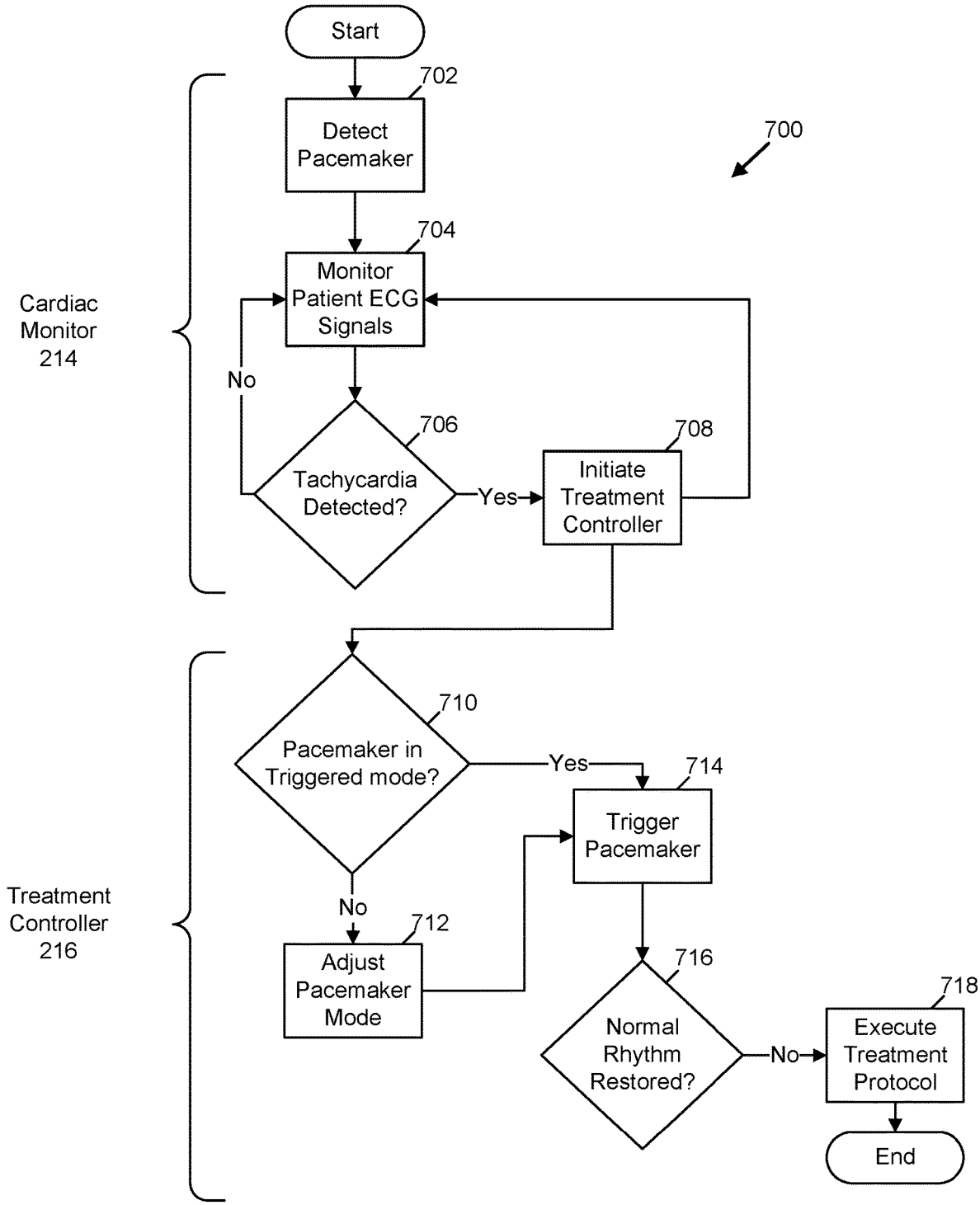
FIG. 7 depicts another monitoring and treatment process in accordance with at least one example disclosed herein.

FIG. 2 illustrates a sample component-level view of the medical device controller 120. As shown in FIG. 2, the medical device controller 120 can include a therapy delivery circuit 202, a data storage 204, a network interface 206, a user interface 208, at least one battery 210, a sensor interface 212, a pacemaker interface 228, an cardiac monitor 214, a treatment controller 216, and least one processor 218. A patient monitoring medical device can include a medical device controller 120 that includes like components as those described above, but does not include the therapy delivery circuit 202 (shown in dotted lines).

The therapy delivery circuit 202 can be coupled to one or more electrodes 220 configured to provide therapy to the patient (e.g., therapy electrodes 114*a-b* as described above in connection with FIG. 1). For example, the therapy delivery circuit 202 can include, or be operably connected to, circuitry components that are configured to generate and provide the therapeutic electrical pulse or shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack, such as the at least one battery 210.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device.

In certain implementations, the user interface 208 can include one or more physical interface devices such as input devices, output devices, and combination input/output devices and a software stack configured to drive operation of the devices. These user interface elements may render visual, audio, and/or tactile content, including content relating to location-specific processing. Thus the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1), heart sounds sensors 224, and tissue fluid monitors 226 (e.g., based on ultra-wide band radiofrequency devices). As such, the sensor interface 212 may include amplifiers and analog to digital converters to condition and digitize signals acquired by the sensors.

The ECG electrodes 222 can monitor a patient's ECG information. For example, the ECG electrodes 222 can be conductive and/or dry electrodes configured to measure changes in a patient's electrophysiology to measure the patient's ECG information. The ECG electrodes 222 can transmit information descriptive of the ECG signals to the sensor interface 212 for subsequent analysis.

The heart sounds sensors 224 can detect a patient's heart sound information. For example, the heart sounds sensors 224 can be configured to detect heart sound values including any one or all of S1, S2, S3, and S4. From these heart sound values, certain heart sound metrics may be calculated, including any one or more of electromechanical activation time (EMAT), percentage of EMAT (% EMAT), systolic dysfunction index (SDI), and left ventricular systolic time (LVST). The heart sounds sensors 224 can include an acoustic sensor configured to detect sounds from a subject's cardiac system and provide an output signal responsive to the detected heart sounds. The heart sounds sensors 224 can also include a multi-channel accelerometer, for example, a three channel accelerometer configured to sense movement in each of three orthogonal axes such that patient movement/body position can be detected and correlated to detected heart sounds information. The heart sounds sensors 224 can transmit information descriptive of the heart sounds information to the sensor interface 212 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if heart data is collected by heart sounds sensor 224 and transmitted to the sensor interface 212, the sensor interface 212 can transmit the data to the processor 218 which, in turn, relays the data to the cardiac monitor 214 and/or the treatment controller 216. This data can also be stored on the data storage 204.

The pacemaker interface 228 can be coupled to an electromagnet 230 (e.g., the electromagnet 118 of FIG. 1) positioned substantially near or over an implanted medical device 232 (e.g., the implanted medical device 116). In some examples, the pacemaker interface 228 can energize the electromagnet using power from the battery 210 to cause the implanted medical device 232 to enter a preprogrammed operational mode. For instance, where the implanted medical device 232 is a pacemaker, the electromagnet 118—when energized—causes the pacemaker to enter, for example, a magnet pacing mode. For example, the pacemaker may respond to an energized electromagnet by switching to, e.g., an asynchronous pacing rate at a preprogrammed atrioventricular (AV) delay and a fixed rate depending on the manufacturer, device model, and the status of the battery. For example, a programmed mode DDD may switch to DOO, or a programmed mode VVI may switch to VOO, and a programmed mode AAI may switch to AOO. If the WCD does not detect any change in the underlying ECG signal of the patient after application of the electromagnet, the WCD can note its inability to detect the pacemaker, log the effort and related information, and continue monitoring the patient's cardiac and other physiological signals. For example, the WCD may not detect any change in pacemaker activity if a pacemaker is absent and/or removed, has a depleted battery (e.g., low battery charge or end of life battery), or programmed to ignore the application of a magnet (e.g., St. Jude, Boston Scientific, and/or Biotronik synchronous modes). As shown in FIG. 2, the pacemaker interface 228 can also be coupled to a wireless antenna to communicate via radio frequency signals (or other signaling methods) with implanted medical device 232 to configure and/or otherwise control the implanted medical device 232.

According to some examples illustrated by FIG. 2, the cardiac monitor 214 is configured to initiate and control monitoring of a patient's cardiac function and identification of arrhythmias experienced by the patient. When executing according to this configuration, in some examples, the cardiac monitor 214 detects arrhythmias by scanning ECG data received from the sensor interface 212 for patterns (e.g. heart rates) indicative of arrhythmias. Responsive to identifying a data pattern indicative of an arrhythmia, the cardiac monitor 214 initiates the pacemaker interface 228 and/or the treatment controller 216. According to various examples, to integrate and/or interoperate with the implanted medical device 232, the cardiac monitor 214 executes various subprocesses that are described further below with reference to FIGS. 3-7.

According to some examples illustrated by FIG. 2, the treatment controller 216 is configured to initiate and control treatment of an arrhythmia identified by the cardiac monitor 214. When executing according to this configuration, in some examples, the treatment controller 216 executes a treatment protocol specific to the particular identified arrhythmia. For instance, the treatment controller 216 may interact with the pacemaker interface 218 to treat a patient experiencing bradycardia or ventricular tachycardia or may pace the patient via the therapy delivery circuit 202 and therapy electrodes 220. In some examples, the treatment controller additionally or alternatively defibrillates the patient where the patient is experiencing atrial or ventricular fibrillation. In some examples, the treatment controller 216 initiates deployment of electrically conductive gel as part of the treatment protocol. Also, in some examples, the treatment controller 216 monitors the reaction of the patient's heart to the treatment protocol and takes further action based on the reaction of the patient's heart. This further action may include altering the treatment protocol, altering the configuration and/or operation of the implanted medical device 232 via the pacemaker interface 228, and/or escalating notifications to external parties. According to various examples, to integrate and/or interoperate with the implanted medical device 232, the treatment controller 216 executes various sub-processes that are described further below with reference to FIGS. 3-5 and 7.

Both the cardiac monitor 214 and the treatment controller 216 can be implemented using hardware or a combination of hardware and software. For instance, in some examples, the cardiac monitor 214 and/or the treatment controller 216 are implemented as software components that are stored within the data storage 204 and executed by the processor 218. In this example, the instructions included in the cardiac monitor 214 and/or the treatment controller 216 can cause the processor 218 to monitor for, detect, and treat arrhythmias. In other examples, the cardiac monitor 214 and/or the treatment controller 216 are application-specific integrated circuits (ASICs) that are coupled to the processor 218 and configured to monitor for, detect, and treat arrhythmias. Thus, examples the cardiac monitor 214 and the treatment controller 216 are not limited to a particular hardware or software implementation.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring, treatment, etc.), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. As referred to herein, the processor 218 can be configured to execute a function where software is stored in a data store coupled to the processor 218, the software being configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

Device Interaction Features

Medical devices in accord with various examples disclosed herein utilize one or more of a variety of features to integrate and/or interoperate with other, distinct medical devices. For instance, with combined reference to FIGS. 1 and 2, some examples are configured to advantageously leverage differences in the construction and disposition of various medical devices to provide a higher, more comprehensive level of care to a patient than the individual medical devices could provide in isolation. When executing according to these configurations in some examples, a medical device (e.g., the medical device 100, which may be a WCD) operates in a monitoring mode and/or a treatment mode. When operating in the monitoring mode, the medical device uses one or more sensing electrodes to acquire ECG signals from a patient's (e.g., the patient 102) heart. Also, while operating in the monitoring mode, a processor (e.g., the at least one processor 218) of the medical device receives, from a sensor interface (e.g., the sensor interface 212), processed ECG data representative of the acquired ECG signals. The processor provides the ECG data to a cardiac monitor (e.g., the cardiac monitor 214). The cardiac monitor processes the ECG data to monitor the patient's cardiac function, to detect the presence of an implantable pacemaker (e.g., the pacemaker 116) implanted within the patient, and/or to monitor the effectiveness of the implanted pacemaker. Should the cardiac monitor determine that the patient is experiencing an arrhythmia condition (e.g., bradycardia, tachycardia, asystole, pulseless electrical activity, atrial flutter, or erratic heart rate), the medical device shifts into the treatment mode. While operating in the treatment mode, the processor provides the ECG data to a treatment controller (e.g., the treatment controller 216). The treatment controller monitors operation of the implanted pacemaker, interoperates with the implanted pacemaker as needed to treat the patient, and/or executes a treatment protocol in which at least one therapy electrode (e.g., the therapy electrodes 114) of the medical device may provide one or more therapeutic stimulation pulses to the patient's heart. Also, within the treatment mode, the treatment controller monitors the patient's heart via the ECG data for a reaction to the one or more therapeutic stimulation pulses. This reaction may include, for example, one or more contractions induced by the therapeutic stimulation pulses and/or contractions induced by internal pacing pulses provided by the pacemaker.

In some examples, the cardiac monitor and the treatment controller are configured to oversee attempts by the implanted pacemaker to successfully execute an ATP protocol and to intervene by providing therapeutic stimulation pulses to the heart of the patient, if appropriate. Example processes executed by the cardiac monitor and the treatment controller in accordance with these configurations are described further below with reference to FIG. 3. When executing according to these examples, the cardiac monitor monitors ECG data and initiates execution of the treatment controller in response to detecting a tachycardia condition affecting the patient's heart. The treatment controller, in turn, monitors the activity of the implanted pacemaker to determine whether the implanted pacemaker successfully restores the patient's heart to a normal condition within a predetermined time period (e.g., see act 314 illustrated in FIG. 3).

The normal condition of the patient's heart and the duration of the predetermined time period may be established during an initial fitting of the medical device. For example, the normal condition of the patient's heart may be recorded as a baseline specific to the patient. In this way, at some examples tailor the monitoring activities to specific idiosyncrasies of the particular patient and, by comparing the current condition of the patient's heart to the baseline, are better able to determine whether the ATP protocol executed by the pacemaker was successful. In some examples, the normal condition of the patient's heart is such that the patient's heart requires some form of regularly pacing by the implanted pacemaker. Thus, in at least some examples, the treatment controller determines whether the patient's heart is restored to a normal condition by identifying that at least one internal pacing pulse issued by the implanted pacemaker resulted in myocardial depolarization. Similarly, the duration of the predetermined time period may default to a particular value (e.g., 60 seconds or some other value between 45 and 75 seconds). In some implementations, a caregiver may specify or adjust the predetermine time period during the initial fitting based on the medical history of the patient and the patient's current physical condition.

In some examples, where the treatment controller determines that the patient's heart is not restored to a normal condition within the predetermined time period, the treatment controller may execute one or more of several preprogrammed actions. For instance, the treatment controller may issue an alert if the treatment controller determines that the implanted pacemaker was unable to restore the patient's heart to a normal condition within the predetermined time period. Alternatively or additionally, the treatment controller may provide one or more transthoracic therapeutic stimulation pulses to the patient's heart. The pulses may include one or more defibrillation pulses.

In some examples, the cardiac monitor may determine whether an implanted pacemaker is disposed within the patient using a variety of systems, devices, and techniques. For instance, in some examples, the cardiac monitor determines whether the patient has an implanted pacemaker by referring to one or more values of one or more configurable parameters stored in the data storage 204. Values of configurable parameters may be assigned, for example, by a healthcare provider, via a user interface (e.g., the user interface 208) during an initial fitting of the medical device to the patient. Alternatively or additionally, in some examples, the cardiac monitor 214 is configured to search for and detect an implanted pacemaker via a pacemaker interface (e.g., the pacemaker interface 228). When executing according to this configuration in one example, the cardiac monitor energizes an electromagnet (e.g., the electromagnet 118) proximal to the implanted pacemaker and monitors the ECG data for a heart rate that matches the magnet rate, noise reversion rate, or interference rate of one or more pacemakers. In this example, where the heart rate equals one of these target rates for a particular brand of pacemaker (e.g., St. Jude, Boston Scientific, Medtronic and/or Biotronik brand pacemakers), the cardiac monitor records that particular pacemaker as being implanted within the patient by manipulating the values of the configurable parameters.

Figure 8:
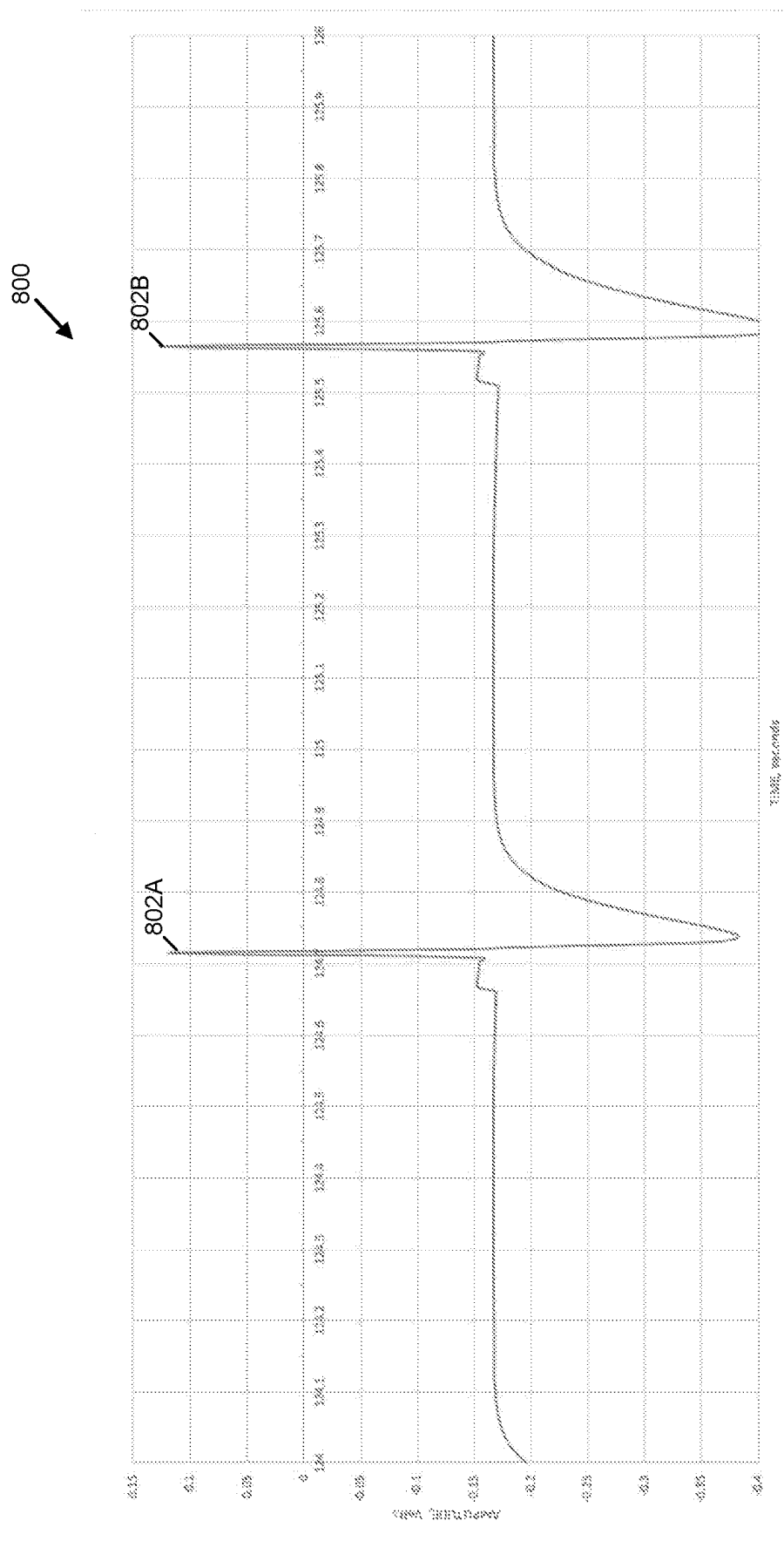
FIG. 8 is a graph illustrating pacing pulse spikes in accordance with at least one example disclosed herein.

In some examples, the cardiac monitor may also detect the presence of an implanted pacemaker by analyzing ECG data in search of pacing pulse spikes. FIG. 8 is a graph 800 of ECG data including two pacing pulse spikes 802A and 802B. The cardiac monitor may detect the presence of pacing pulse spikes such as the pacing pulse spikes 802A and 802B by using a derivative based slope detector and/or an amplitude threshold monitor. In these examples, the cardiac monitor records the presence of the implanted pacemaker by, for example, manipulating the values of the configurable parameters described above.

In examples where the medical device includes the pacemaker interface that includes a radio frequency antenna, or some other wireless transmit and receive device, the treatment controller may be configured to signal the implanted pacemaker to enter an ATP pacing mode. This signaling make be programmed to occur prior to other preprogrammed actions and, in fact, may be programmed to occur prior to expiration of the predetermined time period, if the treatment controller detects that the pacemaker does not appear to be executing an ATP protocol despite the cardiac monitors detection of the tachycardia condition. In some examples, the treatment controller may be additionally or alternatively configured to adjust the pacing mode of the pacemaker and/or the characteristics of pacing pulses provided by the pacemaker in response to expiration of the predetermined time period and failure by the pacemaker to restore the patient's heart to a normal condition. The characteristics of the pacing pulses that may be altered in this way include the pulse waveform, the pulse energy level, the pulse rate, and the pulse width.

In some examples, the cardiac monitor and the treatment controller are configured to monitor the activity of the implanted pacemaker to discriminate between actual arrhythmia conditions being experienced by the patient and artifacts that appear to be arrhythmia conditions. Example processes executed by the cardiac monitor and the treatment controller in accordance with these configurations are described further below with reference to FIG. 4. When executing according to these examples, the cardiac monitor processes ECG data to identify patterns in the ECG data indicative of an arrhythmia condition. In response to detecting the arrhythmia condition, the cardiac monitor initiates execution of the treatment controller. The treatment controller monitors the ECG data for internal pacing pulses provided by the implanted pacemaker and determines and records that the arrhythmia is actual, but not currently treatable by the medical device, where such pacing pulses are present within a predetermined time period (e.g., see act 410 illustrated in FIG. 4). The duration of the predetermined time period may default to a particular value (e.g., 10 seconds, some other value between 3 and 45 seconds, or between 3 and 60 seconds). A caregiver may also specify or adjust the predetermined time period during an initial fitting of the medical device based on the medical history of the patient and the patient's current physical condition. However, if pacing pulses are not present within the predetermined time period, the treatment controller records the arrhythmia as suspect, but treatable by the medical device, and executes an appropriate treatment protocol. The treatment protocol may include provision of one or more alerts.

In some examples wherein the implanted pacemaker is a dual chamber pacemaker, the cardiac monitor and the treatment controller are configured to receive atrial and ventricular ECG data from the implanted pacemaker via the pacemaker interface and identify an arrhythmia using the atrial and ventricular ECG data. Example processes executed by the cardiac monitor and the treatment controller in accordance with these configurations are described further below with reference to FIG. 5. When executing according to these examples, the cardiac monitor uses the enhanced specificity of the ECG data to detect, for example, atrioventricular dissociation. Further, the cardiac monitor uses the atrial and ventricular ECG data to classify detected arrhythmias. For instance, in some examples, the cardiac monitor classifies arrhythmias as tachycardias where the atrial ECG data indicates an atrial beat rate of between 60 and 100 beats per minute (bpm) and the ventricular ECG data indicates a ventricular beat rate of between 110 and 250 bmp. In some examples, the cardiac monitor classifies arrhythmias as fibrillations where the atrial ECG data indicates an atrial beat rate of between 60 and 100 bpm and the ventricular ECG data indicates a ventricular beat rate of between 300 and 600 bmp. In some examples, the cardiac monitor classifies arrhythmias as supraventricular tachycardias where the atrial ECG data indicates an atrial beat rate of between 150 and 250 bpm and the ventricular ECG data indicates a ventricular beat rate of between 150 and 250 bmp. After classifying the arrhythmia, the cardiac monitor initiates execution of the treatment controller.

In some examples, where the cardiac monitor classifies an arrhythmia as a tachycardia, the treatment controller monitors the patient's ECG data to determine whether the pacemaker is able to restore the patient's heart to a normal condition within a predetermined time period. The duration of the predetermined time period may default to a particular value (e.g., 60 seconds or some other value between 45 and 75 seconds) and may be adjusted by the caregiver during an initial fitting of the medical device based on the medical history of the patient and the patient's current physical condition. Where the treatment controller determines that the pacemaker is unable to restore the patient's heart to a normal condition within the predetermined time period, the treatment controller executes a treatment protocol culminating in one or more therapeutic stimulation pulses to the patient's heart. In some examples, where the cardiac monitor classifies an arrhythmia as a fibrillation, the treatment controller immediately executes a treatment protocol culminating in one or more therapeutic stimulation pulses (e.g., defibrillation pulses) to the patient's heart.

In some examples, the cardiac monitor is configured to monitor the activity of the implanted pacemaker to determine whether the implanted pacemaker is in need of maintenance. Example processes executed by the cardiac monitor in accordance with these configurations are described further below with reference to FIG. 6. When executing according to these examples, the cardiac monitor processes ECG data to identify patterns in the ECG data indicative of maintenance conditions. In response to detecting a maintenance condition, the cardiac monitor provides one or more notifications to one or more recipients. These recipients may include the patient, a caregiver, and/or other external entities such as persons or systems. The maintenance conditions that may be detected in these examples include maintenance conditions associated with remaining runtime of a battery powering the implanted pacemaker (e.g., the runtime being below a predetermined value); maintenance conditions associated with lead displacement or wire fracture, which result in failure of the implanted pacemaker to initiate myocardial depolarization via internal pacing pulses; maintenance conditions associated with oversensing intrinsic heart activity, which result in lack of provision of needed pacing pulses; and maintenance conditions associated with undersensing intrinsic heart activity, which result in provision of unneeded pacing pulses.

In some examples where the implanted pacemaker is configured in triggered mode (e.g., VVT), the cardiac monitor and the treatment controller are configured to drive an implanted pacemaker to execute an ATP protocol and to intervene by providing therapeutic stimulation pulses to the heart of the patient, if appropriate. Example processes executed by the cardiac monitor and the treatment controller in accordance with these configurations are described further below with reference to FIG. 7. When executing according to these examples, the cardiac monitor monitors ECG data and initiates execution of the treatment controller in response to detecting a tachycardia condition affecting the patient's heart. The treatment controller, in turn, provides a pulse train of subtherapeutic stimulation pulses to the patient's chest wall. Because the implanted pacemaker is configured in triggered mode, each of the pulses in the pulse train is detected by the implanted pacemaker and results in the implanted pacemaker providing a corresponding internal pacing pulse to the patient's heart.

These pulse trains may have varied characteristics. For instance, in some examples, the treatment controller may determine a tachycardia rate of the tachycardia condition detected by the cardiac monitor and may provide a pulse train to the chest wall at a rate that is between 80% and 90% of the tachycardia rate. In addition, the treatment controller may provide a pulse train including between 5 and 20 pulses within the predetermined time period.

In some examples, where the treatment controller determines that the patient's heart is not restored to a normal condition within the predetermined time period, the treatment controller may execute one or more of several preprogrammed actions. For instance, the treatment controller may issue an alert if the treatment controller determines that the implanted pacemaker was unable to restore the patient's heart to a normal condition within the predetermined time period. Alternatively or additionally, the treatment controller may provide one or more transthoracic therapeutic stimulation pulses to the patient's heart. The pulses may include one or more defibrillation pulses.

Prophylactic WCD with an Implanted Pacemaker Executing ATP

As explained above, in some examples a WCD is used as a prophylactic measure to enable an implanted pacemaker to execute safely an ATP protocol. In these examples, the cardiac monitor and the treatment controller of the WCD are configured to execute jointly a monitoring and treatment process 300 illustrated in FIG. 3.

The monitoring and treatment process 300 starts in the act 302 with the cardiac monitor detecting the presence of an implanted pacemaker. As explained above, the cardiac monitor may detect the presence of the implanted pacemaker using a variety of systems, devices, and techniques which include reading one or more values of one or more parameters configured during an initial fitting of the WCD and/or interacting with the implanted pacemaker via the pacemaker interface.

In act 304 the cardiac monitor monitors ECG data representative of ECG signals acquired by the sensing electrodes of the WCD. In act 306, the cardiac monitor determines whether the ECG data indicates that the patient is experiencing a tachycardia condition. If so, the cardiac monitor calls the treatment controller to initiate its execution in act 308. If the cardiac monitor does not detect a tachycardia condition in the act 306, the cardiac monitor returns to the act 304.

In act 310, the treatment controller determines whether the implanted pacemaker is configured to execute an ATP protocol. The treatment controller may make this determination by reading one or more values of one or more parameters configured during an initial fitting of the WCD and/or interacting with the implanted pacemaker via the pacemaker interface. If, in the act 310, the treatment controller determines that the implanted pacemaker is configured to execute an ATP protocol, the treatment controller executes act 314. If, in the act 310, the treatment controller determines that the implanted pacemaker is not configured to execute an ATP protocol, the treatment controller executes the act 312.

In act 312, the treatment controller adjusts the operating mode of the implanted pacemaker to an ATP mode via the pacemaker interface. In act 314, the treatment controller monitors the ECG data over a predetermined period of time (e.g., 60 seconds). This ECG data reflects the patient's intrinsic cardiac activity and/or internal pacing pulses generated by the implanted pacemaker. By monitoring the ECG data, the treatment controller can track and record the effectiveness of the implanted pacemaker's execution of the ATP protocol during the predetermined period of time. In act 316, the treatment controller determines whether the ECG data indicates that the implanted pacemaker's execution of an ATP protocol successfully restored the heart of the patient to a normal cardiac rhythm within the predetermined time period. It is appreciated that each patient may have a distinctive, idiosyncratic normal cardiac rhythm. As such, some examples of the treatment controller compare (e.g., via a convolution operation) the ECG data to a baseline recorded for the patient during an initial fitting of the WCD. If, in the act 316, the treatment controller determines that the implanted pacemaker successfully restored the patient's heart to a normal condition (i.e., a cardiac rhythm that is normal for the patient), the treatment controller terminates processing. If, in the act 316, the treatment controller determines that the implanted pacemaker did not successfully restore the patient's heart to a normal condition, the treatment controller executes act 318.

In the act 318, the treatment controller adjusts, via the pacemaker interface, one or more characteristics of the internal pacing pulses to be delivered by the implanted pacemaker. The characteristics of the internal pacing pulses that may be altered in this way include the pulse waveform, the pulse energy level, the pulse rate, and the pulse width. For example, the treatment controller may increase the pulse energy level in an attempt to induce myocardial depolarization of the patient's heart according to a predetermined anti-tachycardia rate.

In act 320, the treatment controller again determines whether the ECG data indicates that the implanted pacemaker's execution of an ATP protocol successfully restored the heart of the patient to a normal cardiac rhythm. If, in the act 320, the treatment controller determines that the implanted pacemaker successfully restored the patient's heart to a normal condition, the treatment controller terminates processing. If, in the act 320, the treatment controller determines that the implanted pacemaker did not successfully restore the patient's heart to a normal condition, the treatment controller executes act 322.

In act 322, due to the implanted pacemaker's inability to successfully treat the patient's tachycardia condition, the treatment controller executes a treatment protocol. For instance, where the patient is still experiencing a tachycardia condition, the treatment protocol executed by the WCD may culminate in an overdrive pacing pulse train and/or one or more defibrillation pulses. When executing this treatment protocol, the treatment controller may coordinate and control various components of the WCD to provide the treatment to the patient. For example, the treatment controller may sound an alarm or otherwise notify the patient, bystanders, and/or local or remote caregivers that treatment of the patient is imminent. If the notifications are not answered in a predetermined manner to delay treatment, the treatment controller next signals gel dispensers to dispense electrically conductive gel between the skin of the patient and the therapy electrodes. These gel dispensers may be housed in therapy pads that also house the therapy electrodes. In executing the treatment protocol, the treatment controller next signals discharge circuitry (e.g., the therapy delivery circuit 202) included in the WCD provide one or more transcutaneous therapeutic stimulation pulses, such as pacing pulses and/or defibrillating shocks, to the patient's heart via the therapy electrodes.

In act 324, the treatment controller determines whether the ECG data indicates that the treatment protocol executed in the act 322 successfully restored the heart of the patient to a normal cardiac rhythm. If, in the act 324, the treatment controller determines that the treatment protocol successfully restored the patient's heart to a normal condition, the treatment controller terminates processing. If, in the act 324, the treatment controller determines that the treatment protocol did not successfully restore the patient's heart to a normal condition, the treatment controller executes act 326.

In the act 326, the treatment controller determines whether treatment of the patient should continue. For example, within the act 326, the treatment controller may determine whether execution of the treatment protocol has continued for longer than a predetermined duration or for more than a predetermined number of cycles. Also, within the act 326, the treatment controller may determine whether the medical device has sufficient resources available to continue execution of the treatment protocol (e.g., whether sufficient battery power remains). If, in the act 326, the treatment controller determines that treatment of the patient should not continue, the treatment controller terminates processing. If, in the act 326, the treatment controller determines that treatment of the patient should continue, the treatment controller proceeds to act 328.

In the act 328, the treatment controller determines whether any adjustments to the treatment protocol should be made. For example, within the act 328, the treatment controller may analyze the ECG data to determine adjustments to make to the characteristics of therapeutic stimulation pulses provided by the therapy electrode. These characteristics may include level of current, pulse width, pulse rate, and waveform among other characteristics. Adjustments identified with in the act 328 may be based on an inability of the treatment protocol to capture, cardiovert, or defibrillate the patient, and thus may include increasing the level of current and/or pulse width. After appropriately adjusting the treatment protocol, the treatment controller returns to the act 322 and continues to treat the patient.

Arrhythmia Classification

As explained above, in some examples a WCD monitors the activity of an implanted pacemaker to classify arrhythmias as either being suspect, but treatable by the WCD, or actual, but not presently treatable by the WCD. In these examples, the cardiac monitor and the treatment controller of the WCD are configured to execute jointly a monitoring and treatment process 400 illustrated in FIG. 4.

The monitoring and treatment process 400 starts in the act 402 with the cardiac monitor detecting the presence of an implanted pacemaker as described above. In act 404, the cardiac monitor monitors ECG data representative of ECG signals acquired by the sensing electrodes of the WCD. In act 406, the cardiac monitor determines whether the ECG data indicates that the patient is experiencing an arrhythmia. If so, the cardiac monitor calls the treatment controller to initiate its execution in act 408. If the cardiac monitor does not detect an arrhythmia in the act 406, the cardiac monitor returns to the act 404.

In act 410, the treatment controller monitors the ECG data over a predetermined period of time (e.g., 10 seconds). This ECG data reflects the patient's intrinsic cardiac activity and/or internal pacing pulses generated by the implanted pacemaker. By monitoring the ECG data, the treatment controller can determine whether the implanted pacemaker has detected an arrhythmia, which increases the likelihood that the arrhythmia detected by the cardiac monitor is an actual arrhythmia. In act 412, the treatment controller determines whether the ECG data includes pacing pulse spikes, as described above with reference to FIG. 8. If so, the treatment controller determines that the implanted pacemaker executes act 414. If the treatment controller determines that the ECG data does not include pacing pulse spikes, the treatment controller executes act 418.

In the act 414, the treatment controller records the arrhythmia as suspect, but treatable by the WCD. In act 416, the treatment controller executes one or more treatment protocols which may issue various alerts and provide therapeutic stimulation pulses (e.g., pacing and or defibrillating pulses) as various described herein. These treatment protocols may be adjusted and limited as described above with reference to the acts 324, 326, and 328. In the act 418, the treatment controller records the arrhythmia as actual, but presently untreatable by the WCD.

As explained above, in some examples a WCD interfaces with a dual chamber implanted pacemaker to classify and potentially treat a variety of arrhythmias. In these examples, the cardiac monitor and the treatment controller of the WCD are configured to execute jointly a monitoring and treatment process 500 illustrated in FIG. 5.

The monitoring and treatment process 500 starts in the act 502 with the cardiac monitor detecting the presence of an implanted pacemaker as described above. In act 504, the cardiac monitor monitors atrial and ventricular ECG data representative of atrial and ventricular ECG signals acquired by sensing leads of the dual chamber implanted pacemaker. The atrial and ventricular ECG data may be received from the dual chamber implanted pacemaker via the pacemaker interface. In act 506, the cardiac monitor determines whether the atrial and ventricular ECG data indicates that the patient is experiencing an arrhythmia classifies the arrhythmia, if one is present. For example, the cardiac monitor may classify the arrhythmia as tachycardia where the atrial rate is between 60 and 100 beats per minute (bpm) and the ventricular rate is between 110 and 250 bpm. Alternatively, the cardiac monitor may classify the arrhythmia as fibrillation where the atrial rate is between 60 and 100 bpm and the ventricular rate is between 300 and 600 beats per minute. Alternatively, the cardiac monitor may classify the arrhythmia as supraventricular tachycardia where the atrial rate and the ventricular rate are each between 150 and 250 bpm. If, in the act 506, the cardiac monitor detects an arrhythmia, the cardiac monitor calls the treatment controller to initiate its execution in act 508. If the cardiac monitor does not detect an arrhythmia in the act 506, the cardiac monitor returns to the act 504.

In act 510, the treatment controller monitors the ECG data over a predetermined period of time. The duration of this period of time may vary based on the type of arrhythmia detected in act 506. For instance, the duration may range from about 3 seconds to about 60 seconds where the arrhythmia detected was a fibrillation, may range from about 3 seconds to about 120 seconds or more where the arrhythmia detected is a tachycardia. Monitoring the patient's ECG for other predetermined durations may be possible. For example, the treatment controller may continue to monitor the patient's ECG data for the duration that an arrhythmia is detected, and stop monitoring when normal sinus rhythm is sustained for a predetermined amount of time (e.g., for at least 2 minutes, 5 minutes, 10 minutes, or more). These predetermined durations may be specified or adjusted by a caregiver during initial fitting of the device based on the individual patient's medical history and/or other factors. In act 512, the treatment controller determines whether the ECG data indicates that the heart of the patient to has been restored to a normal cardiac rhythm within the predetermined time period. It is appreciated that each patient may have a distinctive, idiosyncratic normal cardiac rhythm. As such, some examples of the treatment controller compare (e.g., via a convolution operation) the ECG data to a baseline recorded for the patient during an initial fitting of the WCD. If, in the act 512, the treatment controller determines that the implanted pacemaker successfully restored the patient's heart to a normal condition (i.e., a cardiac rhythm that is normal for the patient), the treatment controller terminates processing. If, in the act 512, the treatment controller determines that the implanted pacemaker did not successfully restore the patient's heart to a normal condition, the treatment controller executes act 514. In act 514, the treatment controller executes one or more treatment protocols which may issue various alerts and provide therapeutic stimulation pulses (e.g., pacing and or defibrillating pulses) as various described herein. These treatment protocols may be adjusted and limited as described above with reference to the acts 324, 326, and 328.

Maintenance Patterns and Notifications

As explained above, in some examples a WCD monitors the activity of an implanted pacemaker to determine whether the implanted pacemaker is in need of maintenance. In these examples, the cardiac monitor of the WCD is configured to execute a monitoring process 600 illustrated in FIG. 6.

The monitoring process 600 starts in the act 602 with the cardiac monitor detecting the presence of an implanted pacemaker as described above. In act 604, the cardiac monitor monitors ECG data representative of ECG signals acquired by the sensing electrodes of the WCD. In act 606, the cardiac monitor determines whether the ECG data includes a pattern matching one of a plurality of predetermined patterns that indicate the implanted pacemaker requires maintenance. These predetermined patterns may include a train of pacing pulses having a rate equal to a low battery rate for the implanted pacemaker, unnecessary pacing pulses, omitted pacing pulses, and pacing pulses that fail to result in capture (myocardial depolarization). If, in the act 506, the cardiac monitor detects one or more of these predetermined, maintenance patterns in the ECG data, the cardiac monitor issues one or more notifications to one or more recipients in act 608. These one or more recipients may include the patient, a caregiver, and/or other external entities such as persons or systems. The notification issued may include information regarding the required maintenance. For example, where the maintenance pattern identified is a pulse train having a rate equal to a low battery rate of the implanted pacemaker, the notification may indicate that the battery of the implanted pacemaker is low on power. Where the maintenance pattern identified is unnecessary pacing pulses, the notification may indicate that the implanted pacemaker is undersensing intrinsic heart activity. Where the maintenance pattern identified is omitted pacing pulses, the notification may indicate that the implanted pacemaker is oversensing intrinsic heart activity. Where the maintenance pattern identified is lack of capture, the notification may indicate that lead displacement or wire fracture. If the cardiac monitor does not detect a maintenance pattern in the act 606, the cardiac monitor returns to the act 604.

WCD Using Triggered Mode to Device ATP Via an Implanted Pacemaker

As explained above, in some examples a WCD is drives an implanted pacemaker configured to operate in triggered mode to execute of an ATP protocol. In these examples, the cardiac monitor and the treatment controller of the WCD are configured to execute jointly a monitoring and treatment process 700 illustrated in FIG. 7.

The monitoring and treatment process 700 starts in the act 702 with the cardiac monitor detecting the presence of an implanted pacemaker as described above. In act 704 the cardiac monitor monitors ECG data representative of ECG signals acquired by the sensing electrodes of the WCD. In act 706, the cardiac monitor determines whether the ECG data indicates that the patient is experiencing a tachycardia condition. If so, the cardiac monitor calls the treatment controller to initiate its execution in act 708. If the cardiac monitor does not detect a tachycardia condition in the act 706, the cardiac monitor returns to the act 704.

In act 710, the treatment controller determines whether the implanted pacemaker is configured to operate in a triggered mode. The treatment controller may make this determination by reading one or more values of one or more parameters configured during an initial fitting of the WCD and/or interacting with the implanted pacemaker via the pacemaker interface. If, in the act 710, the treatment controller determines that the implanted pacemaker is configured to operate in a triggered mode, the treatment controller executes act 714. If, in the act 710, the treatment controller determines that the implanted pacemaker is not configured to operate in a triggered mode, the treatment controller executes the act 712.

In act 712, the treatment controller adjusts the operating the mode of the implanted pacemaker to a triggered mode via the pacemaker interface. In act 714, the treatment controller provides one or more subtherapeutic stimulation pulses to the chest wall of the patent via the therapy electrodes of the WCD. These subtherapeutic stimulation pulse may be detected by the implanted pacemaker. When operating in triggered mode, the implanted pacemaker issues an internal pacing pulse in response to detecting each subtherapeutic stimulation pulse. In this way, the treatment controller drives the implanted pacemaker to execute an ATP protocol. In some examples, the treatment controller determines an antitachycardia pacing rate and issues the one or more subtherapeutic stimulation pulses in accordance with this antitachycardia pacing rate. For instance, the one or more subtherapeutic stimulation pulses may include 5 to 20 pulses (each resulting in an internal pacing pulse) issued at a rate that is between 80% and 90% of the tachycardia rate.

In act 716, the treatment controller determines whether the ECG data indicates that the implanted pacemaker's execution of an ATP protocol successfully restored the heart of the patient to a normal cardiac rhythm. It is appreciated that each patient may have a distinctive, idiosyncratic normal cardiac rhythm. As such, some examples of the treatment controller compare (e.g., via a convolution operation) the ECG data to a baseline recorded for the patient during an initial fitting of the WCD. If, in the act 716, the treatment controller determines that the implanted pacemaker successfully restored the patient's heart to a normal condition (i.e., a cardiac rhythm that is normal for the patient), the treatment controller terminates processing. If, in the act 716, the treatment controller determines that the implanted pacemaker did not successfully restore the patient's heart to a normal condition, the treatment controller executes act 718. In the act 718, the treatment controller executes one or more treatment protocols which may issue various alerts and provide therapeutic stimulation pulses (e.g., pacing and or defibrillating pulses) as various described herein. These treatment protocols may be adjusted and limited as described above with reference to the acts 324, 326, and 328.

ADDITIONAL EXAMPLES

Several examples incorporate various combinations of the features described above to advantageous effect. For instance, in some examples, the arrhythmia classification features described herein may be combined with the prophylactic WCD to enable a WCD to both verify that a suspect tachycardia condition is an actual tachycardia condition and to oversee the implanted pacemaker's execution of an ATP protocol. Additionally, it is appreciated that at least some of the features described herein are optional and may not be present in every example. For instance, some examples do not attempt to detect the presence of implanted pacemakers or alter the operating modes of implanted pacemakers via a pacemaker interface.

Although the subject matter contained herein has been described in detail for the purpose of illustration, it is to be understood that such detail is solely for that purpose and that the present disclosure is not limited to the disclosed examples, but, on the contrary, is intended to cover modifications and equivalent arrangements that are within the scope of the appended claims. For example, it is to be understood that the present disclosure contemplates that, to the extent possible, one or more features of any example can be combined with one or more features of any other example.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

The invention claimed is:

1. An ambulatory medical device comprising:
   a garment to be worn by a patient prescribed the ambulatory medical device for an extended period of time, the extended period of time comprising at least one week;
   at least one sensing electrode affixed to the garment when the garment is worn by the patient, the at least one sensing electrode configured to acquire external electrocardiogram (ECG) signals from the patient;
   at least one therapy electrode affixed to the garment when the garment is worn by the patient, the at least one therapy electrode configured to couple externally to a skin of the patient and to provide one or more therapeutic stimulation pulses to a heart of the patient;
   a patient interface configured to receive at least one input from the patient;
   an implanted device interface configured to communicate with an implanted cardiac device implanted within the patient;
   at least one processor coupled to the at least one sensing electrode, the at least one therapy electrode, the patient interface, and the implanted device interface and configured to
      receive, from the implanted cardiac device via the implanted device interface, atrial ECG data descriptive of atrial heart activity,
      receive, from the implanted cardiac device via the implanted device interface, ventricular ECG data descriptive of ventricular heart activity, identify an arrhythmia condition based on analysis of the atrial ECG data and the ventricular ECG data received from the implanted cardiac device, generate at least one alert directed to the patient indicating the arrhythmia condition, the alert comprising a notification that delivery of the one or more therapeutic stimulation pulses is imminent, and if no response to the alert is received from the patient via the patient interface to delay treatment, provide the one or more therapeutic stimulation pulses to the heart of the patient; and a user interface operably connected to the at least one processor and configured to provide the alert to the patient.

2. The ambulatory medical device of claim 1, wherein the atrial ECG data and the ventricular ECG data indicate atrioventricular dissociation.

3. The ambulatory medical device of claim 2, wherein the at least one processor is configured to identify the arrhythmia condition as a tachycardia condition where the atrial ECG data indicates a beat rate between 60 beats per minute and 100 beats per minute and the ventricular ECG data indicates a beat rate between 110 beats per minute and 250 beats per minute.

4. The ambulatory medical device of claim 3, wherein the at least one processor is configured to:
   determine, in response to detecting the tachycardia condition, whether the implanted cardiac device restored the heart of the patient to a normal condition within a predetermined period; and
   provide the one or more therapeutic stimulation pulses to the heart of the patient in response to determining that the implanted cardiac device failed to restore the heart of the patient to the normal condition within the predetermined period.

5. The ambulatory medical device of claim 4, wherein the predetermined period is 60 seconds.

6. The ambulatory medical device of claim 2, wherein the at least one processor is further configured to:
   identify the arrhythmia condition as a fibrillation condition where the atrial ECG data indicates a beat rate between 60 beats per minute and 100 beats per minute and the ventricular ECG data indicates a beat rate between 300 beats per minute and 600 beats per minute; and
   provide, in response to identifying the fibrillation condition, the one or more therapeutic stimulation pulses to the heart of the patient via the at least one therapy electrode.

7. The ambulatory medical device of claim 1, wherein the at least one processor is further configured to determine whether the implanted cardiac device restored the heart of the patient to a normal condition at least in part by comparing the atrial ECG data and the ventricular ECG data to a baseline of the heart of the patient recorded during an initial fitting of the ambulatory medical device to the patient.

8. The ambulatory medical device of claim 1, wherein the at least one processor is configured to determine whether the implanted cardiac device restored the heart of the patient to a normal condition at least in part by identifying at least one internal pacing pulse provided by the implanted cardiac device and determining whether the at least one internal pacing pulse resulted in myocardial depolarization.

9. The ambulatory medical device of claim 1, wherein the at least one processor is further configured to transmit an instruction to reconfigure the implanted cardiac device via the interface in response to the implanted cardiac device having failed to restore the heart of the patient to a normal condition within a predetermined period.

10. The ambulatory medical device of claim 9, wherein the instruction to reconfigure comprises an instruction to alter at least one characteristic of at least one internal pacing pulse.

11. The ambulatory medical device of claim 10, wherein the at least one characteristic comprises at least one of a pulse waveform, a pulse energy level, a pulse rate, and a pulse width.

12. The ambulatory medical device of claim 1, wherein the one or more therapeutic stimulation pulses comprises at least one defibrillation shock.

13. The ambulatory medical device of claim 1, wherein the at least one processor is further configured to identify the arrhythmia condition as a supraventricular tachycardia condition where the atrial ECG data indicates a beat rate between 150 beats per minute and 250 beats per minute and the ventricular ECG data indicates a beat rate between 150 beats per minute and 250 beats per minute.

14. The ambulatory medical device of claim 1, wherein the extended period of time comprises at least one of one week, one month, two months, three months, or six months.

15. The ambulatory medical device of claim 1, wherein the patient interface comprises a physical input device configured to receive at least one user input from the patient.

* * * * *